(12) United States Patent
Bausch et al.

US011576916B2

(10) Patent No.: US 11,576,916 B2
(45) Date of Patent: Feb. 14, 2023

(54) METHODS OF PREVENTING OR TREATING OPHTHALMIC DISEASES

(71) Applicant: KINARUS AG, Basel (CH)

(72) Inventors: Alexander Bausch, Riehen (CH); Matthew Wright, Basel (CH)

(73) Assignee: KINARUS AG, Basel (CH)

( * ) Notice: Subject to any disclaimer, the term of this patent is extended or adjusted under 35 U.S.C. 154(b) by 0 days.

(21) Appl. No.: 16/500,504

(22) PCT Filed: Apr. 3, 2018

(86) PCT No.: PCT/EP2018/058486
§ 371 (c)(1),
(2) Date: Oct. 3, 2019

(87) PCT Pub. No.: WO2018/185098
PCT Pub. Date: Oct. 11, 2018

(65) Prior Publication Data
US 2020/0061069 A1    Feb. 27, 2020

(30) Foreign Application Priority Data

Apr. 4, 2017 (EP) .................................... 17164765

(51) Int. Cl.
| | | |
|---|---|---|
| A61K 31/519 | (2006.01) | |
| A61P 27/02 | (2006.01) | |
| A61K 31/4439 | (2006.01) | |
| A61K 9/00 | (2006.01) | |

(52) U.S. Cl.
CPC ........ *A61K 31/519* (2013.01); *A61K 31/4439* (2013.01); *A61P 27/02* (2018.01); *A61K 9/0053* (2013.01)

(58) Field of Classification Search
None
See application file for complete search history.

(56) References Cited

U.S. PATENT DOCUMENTS

| | | |
|---|---|---|
| 2005/0107408 A1 | 5/2005 | Goldstein |
| 2007/0208043 A1 | 9/2007 | Clark et al. |

FOREIGN PATENT DOCUMENTS

| | | |
|---|---|---|
| JP | 2010-235535 A | 10/2010 |
| WO | 02/064594 A2 | 8/2002 |
| WO | 2004/014907 A1 | 2/2004 |
| WO | 2010/048446 A2 | 4/2010 |
| WO | 2015/103480 A1 | 7/2015 |

OTHER PUBLICATIONS

Thurmond et al., Kinetic of small molecule inhibitor binding to p38 kinase. European Journal of Biochemistry, 2001, 268, 5747-5754.*
Kyosseva S. V., Targeting MAPK Signaling in Age-Related Macular Degeneration. Ophthalmology and Eye Diseases. 2016, 8, 23-30.*
Lambert et al., Of Mice and Monkeys: Neuroprotective Efficacy of the p38 inhibitor BIRB 796 Depends on Model Duration in Experimental Glaucoma. Scientific Report, 2020, 10, 1-10.*
Zhang et al., Role of Peroxisome Proliferator-Activated Receptor γ in Ocular diseases. Journal of Ophthalmology, 2015, p. 1-10.*
Pershadsingh et al., PPAR γ Agonists: Potential as Therapeutics for Neovascular Retinopathies. PPAR Research, 2008, p. 1-10.*
Schafer, S., Kolkhof, P. Failure is an option: learning from unsuccessful proof-of-concept trials. Drug Discovery Today. Nov. 2008, 13, 913-916.*
Horig, H., Pullman, W. From bench to clinic and back: Perspective on the 1st IQPC Translational Research conference. Journal of Translational Medicine. Dec. 2004, 2, 44.*
International Search Report, International Application No. PCT/EP2018/058486, dated Jun. 7, 2018, 9 pages.
Boyu et al., "Therapeutic Effect of Fenofibrate on Age Related Macular Degeneration," English Abstract. Annual Meeting of the Association-for-Research-in-Vision-and-Ophthalmology (ARVO), Ft. Lauderdale, Florida, pp. 1-2 (2011).
Choudhary et al., "A Brief Discussion on Lipid Activated Nuclear Receptors and Their Potential Role in Regulating Microglia in Age-Related Macular Degeneration (AMD)," Advances in Experimental Medicine and Biology 854:45-51 (2016).
Del V Cano et al., "PPAR-α Ligands as Potential Therapeutic Agents for Wet Age-Related Macular Degeneration," PPAR Research 2008:1-5 (2008).
Goldstein et al., "Selective p38α Inhibitors Clinically Evaluated for the Treatment of Chronic Inflammatory Disorders," Journal of Medicinal Chemistry 53:2345-2353 (2010).
Ji et al., "PPARγ Agonist Pioglitazone Inhibits Microglia Inflammation by Blocking p38 Mitogen-Activated Protein Kinase Signaling Pathways," Inflammation Research 59:921-929 (2010).
Murata et al., "Peroxisome Proliferator-Activated Receptor-γ Ligands Inhibit Choroidal Neovascularization," Investigative Ophthalmology & Visual Science 41(8): 2309-2317 (2000).
Tamás, F., "A New Possible Strategy for Prevention and Preventative Treatment of Age-Related Macular Degeneration Resting on Recent Clinical and Pathophysiological Observations," English Abstract, Medline 150(11): 1-2 (2009).

* cited by examiner

*Primary Examiner* — Po-Chih Chen
(74) *Attorney, Agent, or Firm* — Medler Ferro Woodhouse Mills PLLC

(57) ABSTRACT

The present invention relates to a pharmaceutical combination comprising:
(a) a PPAR agonist;
(b) a p38 kinase inhibitor; and optionally
(c) one or more pharmaceutically acceptable diluents, excipients or carriers for use in a method of preventing or treating ophthalmic diseases or disorders in a subject.

3 Claims, 2 Drawing Sheets

METHODS OF PREVENTING OR TREATING OPHTHALMIC DISEASES

THE FIELD OF THE INVENTION

The present invention relates to methods of preventing or treating ophthalmic diseases or disorders.

BACKGROUND OF THE INVENTION

Ophthalmic diseases or disorders are often devastating diseases leading to complete or partial blindness. For example, age-related macular degeneration (AMD) is the leading cause of blindness in people 60 years and older in developed countries. A recent systematic review and meta-analysis has shown that 8.7% of the worldwide population has AMD, and with the increase of lifespan the projected number of people with the disease will be at about 196 million in 2020, reaching 288 million in 2040. About 1.75 million Americans are affected by AMD, and this number is expected to grow to almost 3 million by 2020. No therapy is currently available for the dry, slowly progressing atrophic form of AMD. In conclusion, there is a high unmet medical need for the treatment of ophthalmic diseases or disorders, such as AMD.

SUMMARY OF THE INVENTION

It has now unexpectedly been found that a pharmaceutical combination comprising a PPAR agonist, such as pioglitazone and a p38 inhibitor, e.g. a compound of formula I or II as defined hereinbelow, such as pamapimod, is useful for preventing or treating ophthalmic diseases or disorders, in particular macular degeneration, such as AMD.

In addition, it has unexpectedly been found that a compound of formula I or a pharmaceutically acceptable salt thereof (as as defined hereinbelow) alone, i.e. not in combination with a PPAR agonist, is useful for preventing or treating ophthalmic diseases or disorders. In a standard model established in AMD research, it was surprisingly found that treatment with said combination provides a synergistic effect.

Accordingly, in a first aspect, the present invention provides a pharmaceutical combination comprising:
(a) a PPAR agonist;
(b) a p38 kinase inhibitor; and optionally
(c) one or more pharmaceutically acceptable diluents, excipients or carriers for use in a method of preventing or treating ophthalmic diseases or disorders in a subject.

In a further aspect, the present invention provides a compound of formula I

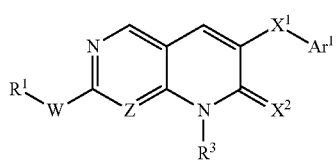

Formula I or a pharmaceutically acceptable salt thereof, wherein
Z is N or CH;
W is $NR^2$;
$X^1$ is O, $NR^4$ (where $R^4$ is hydrogen or alkyl), S, or $CR^5R^6$ (where $R^5$ and $R^6$ are independently hydrogen or alkyl) or C=O;
$X^2$ is O or $NR^7$;
$Ar^1$ is aryl or heteroaryl;
$R^2$ is hydrogen, alkyl, acyl, alkoxycarbonyl, aryloxycarbonyl, heteroalkylcarbonyl, heteroalkyloxycarbonyl or —$R^{21}$—$R^{22}$ where $R^{21}$ is alkylene or —C(=O)— and $R^{22}$ is alkyl or alkoxy;
$R^1$ is hydrogen, alkyl, haloalkyl, aryl, aralkyl, heteroaryl, heteroaralkyl, cycloalkyl, cycloalkylalkyl, heteroalkyl-substituted cycloalkyl, heterosubstituted cycloalkyl, heteroalkyl, cyanoalkyl, heterocyclyl, heterocyclylalkyl, $R^{12}$—$SO_2$-heterocycloamino (where $R^{12}$ is haloalkyl, aryl, aralkyl, heteroaryl or heteroaralkyl), —$Y^1$—C(O)—$Y^2$—$R^{11}$ (where $Y^1$ and $Y^2$ are independently either absent or an alkylene group and $R^{11}$ is hydrogen, alkyl, haloalkyl, hydroxy, alkoxy, amino, monoalkylamino or dialkylamino), (heterocyclyl)(cycloalkyl)alkyl or (heterocyclyl)(heteroaryl)alkyl;
$R^3$ is hydrogen, alkyl, cycloalkyl, cycloalkylalkyl, aryl, aralkyl, haloalkyl, heteroalkyl, cyanoalkyl, alkylene-C(O)—$R^{31}$ (where $R^{31}$ is hydrogen, alkyl, hydroxy, alkoxy, amino, monoalkylamino or dialkylamino), amino, monoalkylamino, dialkylamino or $NR^{32}$—$Y^3$—$R^{33}$ (where $Y^3$ is —C(O), —C(O)O—, —C(O)$NR^{34}$, $S(O)_2$ or $S(O)_2NR^{35}$; $R^{32}$, $R^{34}$ and $R^{35}$ are independently hydrogen or alkyl; and $R^{33}$ is hydrogen, alkyl, cycloalkyl, cycloalkylalkyl, heteroalkyl or optionally substituted phenyl) or acyl; and
$R^7$ is hydrogen or alkyl;
and optionally one or more pharmaceutically acceptable diluents, excipients or carriers for use in a method of preventing or treating ophthalmic diseases or disorders in a subject.

In yet a further aspect, the present invention provides a kit for use in a method of preventing or treating ophthalmic diseases or disorders in a subject, comprising a pharmaceutical combination comprising:
(a) a PPAR agonist;
(b) a p38 kinase inhibitor; and optionally
(c) one or more pharmaceutically acceptable diluents, excipients or carriers; and instructions for using the kit.

DETAILED DESCRIPTION OF THE INVENTION

Figure 1:
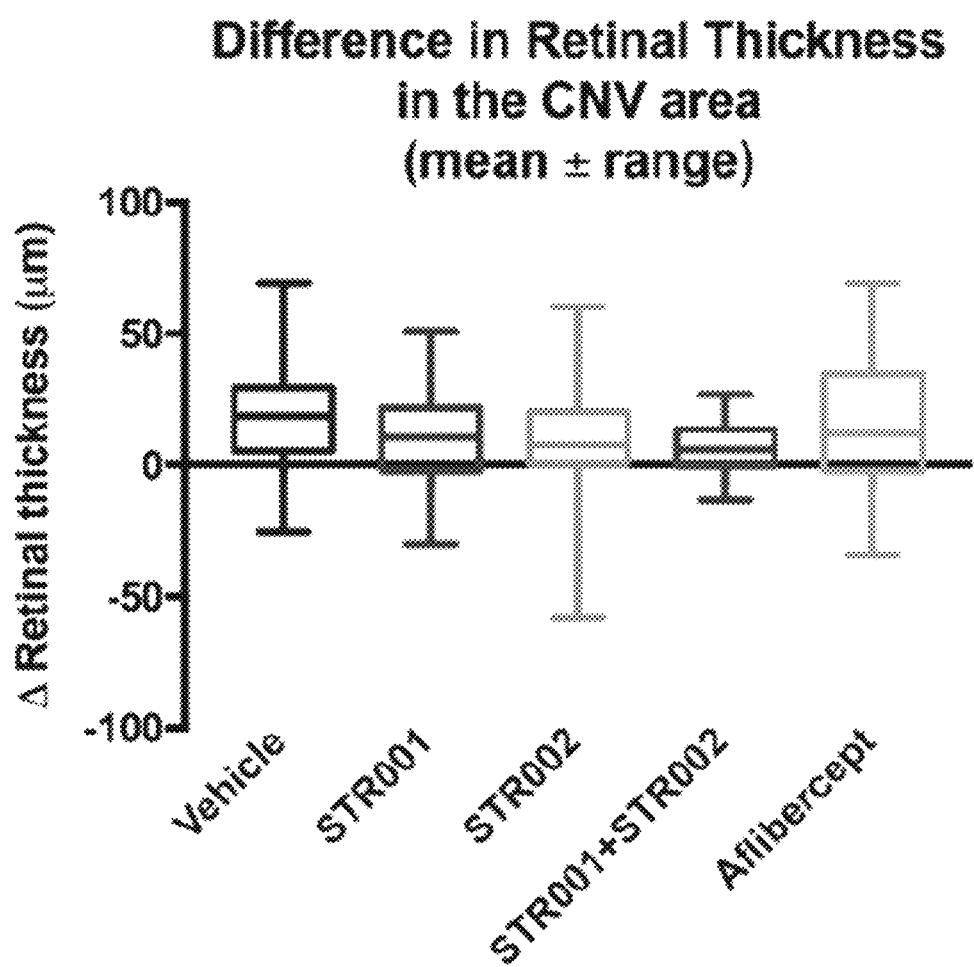
FIG. 1 shows difference in retinal thickness in the CNV area as compared to the total retinal thickness. (STR001=pioglitazone HCl; STR002=pamapimod).

For the purposes of interpreting this specification, the following definitions will apply and whenever appropriate, terms used in the singular will also include the plural and vice versa. It is to be understood that the terminology used herein is for the purpose of describing particular embodiments only and is not intended to be limiting.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any embodiment. The invention extends to any novel one, or any novel combination, of the features disclosed in this specification (including any accompanying claims, abstract and drawings), or to any novel one, or any novel combination, of the steps of any method or process so disclosed.

The terms "comprising", "having", and "including" are to be construed as open-ended terms (i.e., meaning "including, but not limited to") unless otherwise noted.

The term "pharmaceutically acceptable diluents, excipients or carriers" as used herein refers to diluents, excipients or carriers that are suitable for use with humans and/or animals without undue adverse side effects (such as toxicity, irritation, and allergic response) commensurate with a reasonable benefit/risk ratio. "Diluents" are agents which are added to the bulk volume of the active agent making up the solid composition. As a result, the size of the solid composition increases, which makes it easier to handle. Diluents are convenient when the dose of drug per solid composition is low and the solid composition would otherwise be too small. "Excipients" can be binders, lubricants, glidants, coating additives or combinations thereof. Thus, excipients are intended to serve multiple purposes. "Carriers" can be solvents, suspending agents or vehicles, for delivering the instant compounds to a subject.

The term "ophthalmic diseases or disorders" is intended to refer to medical conditions of the eye generally referred to as ophthalmic diseases or disorders and known in the art. Accordingly, the term "ophthalmic diseases or disorders" is meant to include, but is not limited to, diseases or disorders selected from:

disorders of choroid and retina, such as disorders of choroid and retina selected from focal, disseminated and unspecified chorioretinal inflammation, such as chorioretinitis, choroiditis, retinitis, retinochoroiditis, syphilitic chorioretinitis (late), cytomegalovirus retinitis, chorioretinitis due to toxoplasma and tuberculous chorioretinitis; posterior cyclitis, such as pars planitis; Harada's disease; chorioretinal scars, such as macula scars of posterior pole (postinflammatory or post-traumatic) or solar retinopathy; choroidal degeneration, such as atrophy or sclerosis; hereditary choroidal dystrophy, such as choroideremia, central areolar choroidal dystrophy, generalized choroidal dystrophy or peripapillary choroidal dystrophy; choroid gyrate atrophy; choroidal haemorrhage and rupture; and choroidal detachment;

retinal detachments and breaks, such as primary and secondary retinal detachment and retinoschisis; retinal vascular occlusions, such as retinal artery occlusion and retinal vein occlusion;

other retinal disorders, such as retinopathy, e.g. hypertensive retinopathy, retinopathy of prematurity and central serous retinopathy; idiopathic retinopathy, proliferative retinopathy, vitreoretinopathy; vasculopathies associated with telangiectasias or aneurysms; retinopathies associated with lupus erythematosus, rheumatoid arthritis, multiple sclerosis, myasthenia gravis, uveoretinitis or diabetes mellitus; macular degeneration, e.g. age-related macular degeneration (AMD), hereditary macular degeneration (juvenile macular degeneration), such as retinitis pigmentosa (retinopathia pigmentosa), morbus Best, morbus Stargardt and Sorsby's disease, diabetic retinopathy (retinopathia diabetica), myopic macular degeneration, macular degeneration due to inflammation (retinitis), such as presumed ocular histoplasmosis syndrome (POHS) and retinal toxicosis of systemic medications, e.g. chloroquine retinopathy (bull's eye maculopathy); epiretinal membrane; peripheral retinal degeneration; hereditary retinal dystrophy; retinal haemorrhage; separation of retinal layers and macular edema;

glaucoma of all etiologies and manifestations, such as primary and secondary open-angle glaucoma, primary angle-closure glaucoma, glaucoma associated with intraocular infammation, steriod-induced glaucoma, glaucoma associated with intraocular hemorrhage, pseudoexfoliative syndrome and glaucomatous optic neuropathy;

optic neuropathy; and ocular hypertension.

The term "macular degeneration" refers to a group of ophthalmic diseases or disorders and disorders affecting the macula lutea, such as age-related macular degeneration (AMD), hereditary macular degeneration (juvenile macular degeneration) e.g. retinitis pigmentosa (retinopathia pigmentosa), morbus Best, morbus Stargardt, Sorsby's disease, diabetic retinopathy (retinopathia diabetica), myopic macular degeneration, macular degeneration due to inflammation (retinitis) e.g. presumed ocular histoplasmosis syndrome (POHS), and retinal toxicosis of systemic medications, e.g. chloroquine retinopathy (bull's eye maculopathy).

The term "age-related macular degeneration" (AMD) is commonly known by those skilled in the art and is meant to include wet (exudative) AMD and dry (non-exudative) AMD. The term "dry AMD" is meant to include geographic atrophy (GA), which is commonly known by those skilled in the art to be an advanced form of dry AMD.

The term "pharmaceutically acceptable salt" of a compound means a salt that is pharmaceutically acceptable and that it possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxy-benzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo [2.2.2]-oct-2-enel-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g. an alkaline metal ion, an alkaline earth metal ion, or an aluminum ion; or coordinates with an organic base such as ethanolamine, diethanolamine, triethanolamine, tromethamine, N-methylglucamine, and the like. Preferred salts comprise acid addition salts formed with hydrochloric acid.

The terms "subject" and "patient" are used herein interchangeably and refer to mammals, in particular humans.

The term "about" as used herein refers to +/−10% of a given measurement.

In a first aspect, the present invention provides a pharmaceutical combination comprising:
(a) a PPAR agonist;
(b) a p38 kinase inhibitor; and optionally
(c) one or more pharmaceutically acceptable diluents, excipients or carriers for use in a method of preventing or treating ophthalmic diseases or disorders in a subject.

PPAR Agonists

The term "PPAR agonist" as used herein refers to a drug that is activating peroxisome proliferator activated receptor (PPAR) such as PPAR gamma receptor, PPAR alpha receptor, PPAR delta receptor or combinations thereof and includes PPAR gamma agonists such as e.g. pioglitazone, troglitazone or rosiglitazone, PPAR alpha agonists such as e.g. fibrates such as bezafibrate, fenofibrate (fenofibric acid), clofibrate or gemfibrozil, PPAR dual agonists (PPAR alpha/gamma or PPAR alpha/delta agonists) such as e.g. aleglitazar, muraglitazar, tesaglitazar, ragaglitazar, saroglitazar, GFT505 or naveglitazar, PPAR delta agonists such as e.g. GW501516, PPAR pan agonists (PPAR alpha/delta/gamma agonists) or selective PPAR modulators such as e.g. INT131 and the pharmaceutically acceptable salts of these compounds. Usually PPAR gamma agonists, PPAR modulators, PPAR alpha agonists and/or PPAR alpha/gamma dual agonists are used in the pharmaceutical combinations of the present invention, in particular PPAR gamma agonists, PPAR alpha agonists and/or PPAR alpha/gamma dual agonists are used in the pharmaceutical combinations of the present invention, more particularly PPAR gamma agonists and/or PPAR alpha agonists selected from the group consisting of pioglitazone, rosiglitazone, troglitazone, fenofibrate, bezafibrate and pharmaceutically acceptable salts thereof, even more particularly PPAR gamma agonists selected from the group consisting of pioglitazone, rosiglitazone, troglitazone and pharmaceutically acceptable salts thereof, preferably pioglitazone or pharmaceutically acceptable salts thereof. PPAR alpha agonists used in the pharmaceutical combinations of the present invention are selected from the group consisting of bezafibrate, fenofibrate (fenofibric acid), clofibrate, gemfibrozil and pharmaceutically acceptable salts thereof, preferably bezafibrate, fenofibrate (fenofibric acid) or pharmaceutically acceptable salts thereof, more preferably bezafibrate or pharmaceutically acceptable salts thereof. PPAR alpha/gamma dual agonists used in the pharmaceutical combinations of the present invention are selected from the group consisting of aleglitazar, muraglitazar, tesaglitazar, ragaglitazar, saroglitazar, GFT505, naveglitazar and pharmaceutically acceptable salts thereof, preferably muraglitazar, tesaglitazar or pharmaceutically acceptable salts thereof. Preferably PPAR gamma agonists and/or PPAR alpha agonists are used in the pharmaceutical combinations of the present invention, more preferably PPAR gamma agonists or modulators and/or PPAR alpha agonists selected from the group consisting of pioglitazone, rosiglitazone, troglitazone, fenofibrate, bezafibrate, INT131 and pharmaceutically acceptable salts thereof, even more preferably PPAR gamma agonists selected from the group consisting of pioglitazone, rosiglitazone, troglitazone and pharmaceutically acceptable salts thereof are used. Even more preferably, pioglitazone or a pharmaceutically acceptable salt thereof, in particular pioglitazone hydrochloride is used in the pharmaceutical combinations of the present invention. In one embodiment, a thiazolidinedione PPAR agonist is used in the pharmaceutical combinations of the invention. Suitable thiazolidinedione PPAR agonists are for example pioglitazone, troglitazone, rosiglitazone or pharmaceutically acceptable salts thereof. A particularly suitable thiazolidinone PPAR agonist is pioglitazone or a pharmaceutically acceptable salt thereof, in particular pioglitazone hydrochloride.

Pioglitazone is described e.g. in U.S. Pat. No. 4,687,777 or in Dormandy J A, Charbonnel B, Eckland D J, Erdmann E, Massi-Benedetti M, Moules I K, Skene A M, Tan M H, Lefébvre P J, Murray G D, Standl E, Wilcox R G, Wilhelmsen L, Betteridge J, Birkeland K, Golay A, Heine R J, Korányi L, Laakso M, Mokán M, Norkus A, Pirags V, Podar T, Scheen A, Scherbaum W, Schernthaner G, Schmitz O, Skrha J, Smith U, Taton J; PROactive investigators. Lancet. 2005 Oct. 8; 366(9493):1279-89, and is represented by the structural formula indicated below:

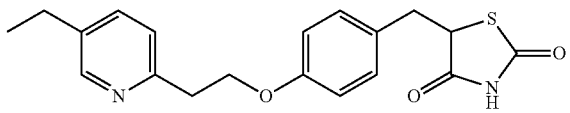 [SMILES: CCc1ccc(CCOc2ccc(CC3SC(=O)NC3=O)cc2)nc1]

Troglitazone is described e.g. in Florez J C, Jablonski K A, Sun M W, Bayley N, Kahn S E, Shamoon H, Hamman R F, Knowler W C, Nathan D M, Altshuler D; Diabetes Prevention Program Research Group. J Clin Endocrinol Metab. 2007 April; 92(4):1502-9 and is represented by the structural formula indicated below:

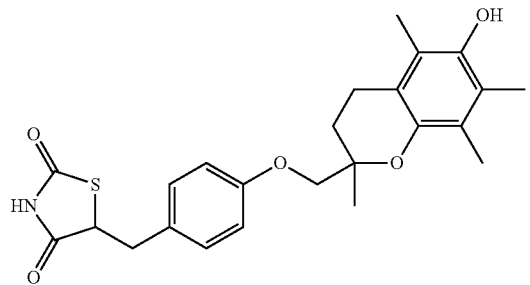 [SMILES: Cc1c(C)c2c(c(C)c1O)CCC(C)(COc1ccc(CC3SC(=O)NC3=O)cc1)O2]

Rosiglitazone is described e.g. in Nissen S E, Wolski K. N Engl J Med. 2007 Jun. 14; 356(24):2457-71. Erratum in: N Engl J Med. 2007 Jul. 5; 357(1):100. Fenofibrate is described e.g. in Bonds D E, Craven T E, Buse J, Crouse J R, Cuddihy R, Elam M, Ginsberg H N, Kirchner K, Marcovina S, Mychaleckyj J C, O'Connor P J, Sperl-Hillen J A. Diabetologia. 2012 June; 55(6):1641-50 and is represented by the structural formula indicated below:

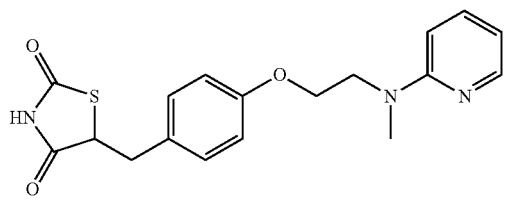 [SMILES: CN(CCOc1ccc(CC2SC(=O)NC2=O)cc1)c1ccccn1]

Bezafibrate is described e.g. in I. Goldenberg, M. Benderly, U. Goldbourt, Vascular health and risk management. 2008, 4(1): 131-141 and is represented by the structural formula indicated below:

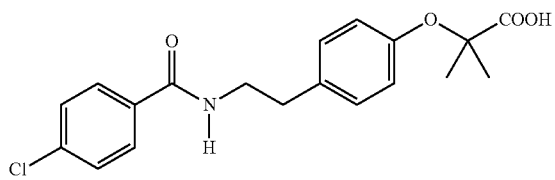 [SMILES: CC(C)(Oc1ccc(CCNC(=O)c2ccc(Cl)cc2)cc1)C(=O)O]

Clofibrate is described e.g. in Rabkin S W, Hayden M, Frohlich J. Atherosclerosis. 1988 October; 73(2-3):233-40 and is represented by the structural formula indicated below:

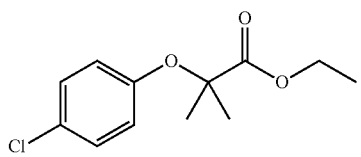 [SMILES: CCOC(=O)C(C)(C)Oc1ccc(Cl)cc1]

Fenofibrate (fenofibric acid) is described e.g. in Schima S M, Maciejewski S R, Hilleman D E, Williams M A, Mohiuddin S M. Expert Opin Pharmacother. 2010 April; 11(5): 731-8 and is represented by the structural formula indicated below:

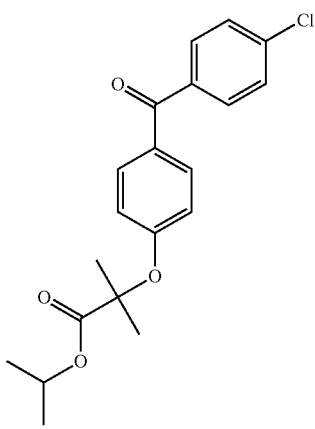 [SMILES: CC(C)OC(=O)C(C)(C)Oc1ccc(C(=O)c2ccc(Cl)cc2)cc1]

Gemfibrozil is described e.g. in Adabag A S, Mithani S, Al Aloul B, Collins D, Bertog S, Bloomfield H E; Veterans Affairs High-Density Lipoprotein Cholesterol Intervention Trial Study Group. Am Heart J. 2009 May; 157(5):913-8 and is represented by the structural formula indicated below:

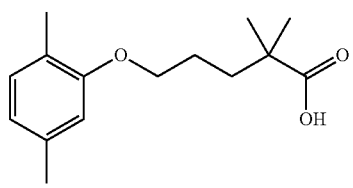 [SMILES: Cc1ccc(C)c(OCCCC(C)(C)C(=O)O)c1]

Aleglitazar is described e.g. in Lincoff A M, Tardif J C, Schwartz G G, Nicholls S J, Rydén L, Neal B, Malmberg K, Wedel H, Buse J B, Henry R R, Weichert A, Cannata R, Svensson A, Volz D, Grobbee D E; AleCardio Investigators. JAMA. 2014 Apr. 16; 311(15):1515-25 and is represented by the structural formula indicated below:

Muraglitazar is described e.g. in Fernandez M, Gastaldelli A, Triplitt C, Hardies J, Casolaro A, Petz R, Tantiwong P, Musi N, Cersosimo E, Ferrannini E, DeFronzo R A. Diabetes Obes Metab. 2011 October; 13(10):893-902 and is represented by the structural formula indicated below:

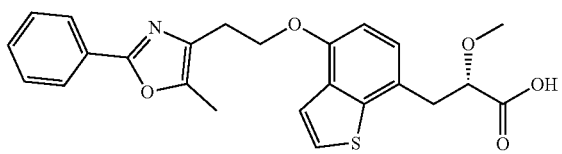 [SMILES: CO[C@@H](Cc1ccc(OCCc2nc(-c3ccccc3)oc2C)c2ccsc12)C(=O)O]

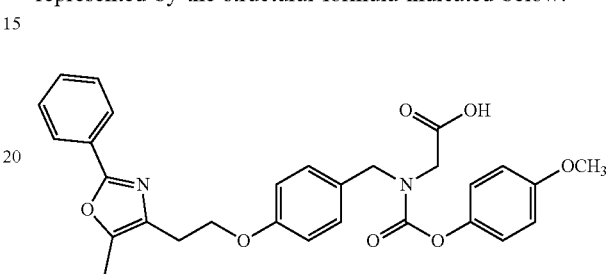

Tesaglitazar is described e.g. in Bays H, McElhattan J, Bryzinski B S; GALLANT 6 Study Group. Diab Vasc Dis Res. 2007 September; 4(3):181-93 and is represented by the structural formula indicated below:

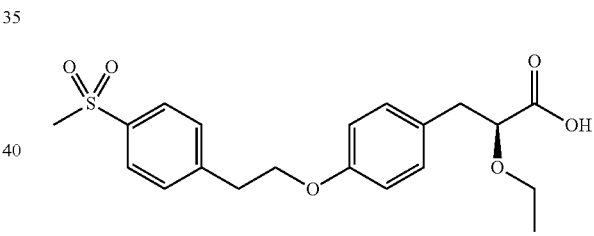

Ragaglitazar is described e.g. in Saad M F, Greco S, Osei K, Lewin A J, Edwards C, Nunez M, Reinhardt R R; Ragaglitazar Dose-Ranging Study Group. Diabetes Care. 2004 June; 27(6): 1324-9 and is represented by the structural formula indicated below:

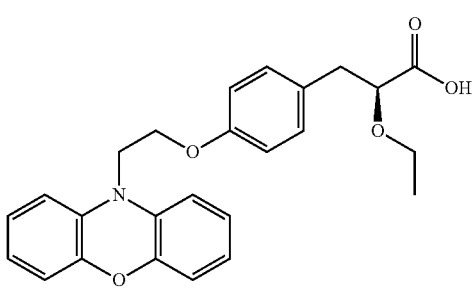 [SMILES: CCO[C@@H](Cc1ccc(OCCN2c3ccccc3Oc3ccccc32)cc1)C(=O)O]

Saroglitazar is described e.g. in Agrawal R. Curr Drug Targets. 2014 February; 15(2):151-5. and is represented by the structural formula indicated below:

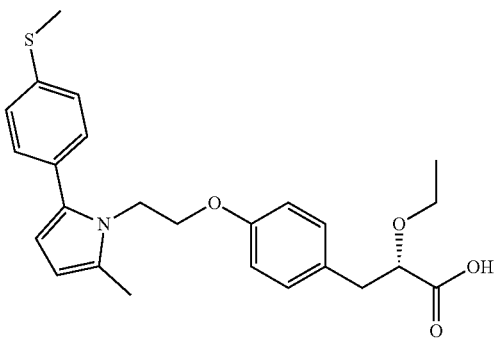 [SMILES: CCO[C@@H](Cc1ccc(OCCn2c(C)ccc2-c2ccc(SC)cc2)cc1)C(=O)O]

Naveglitazar is described e.g. in Ahlawat P, Srinivas N R. Eur J Drug Metab Pharmacokinet. 2008 July-September; 33(3):187-90. GW501516 is described e.g. in Wang X, Sng M K, Foo S, Chong H C, Lee W L, Tang M B, Ng K W, Luo B, Choong C, Wong M T, Tong B M, Chiba S, Loo S C, Zhu P, Tan N S. J Control Release. 2015 Jan. 10; 197:138-47 and is represented by the structural formula indicated below:

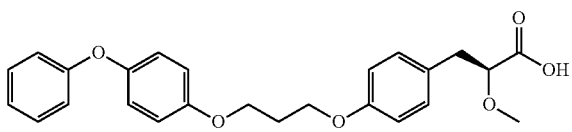 [SMILES: CO[C@@H](Cc1ccc(OCCCOc2ccc(Oc3ccccc3)cc2)cc1)C(=O)O]

GFT505 is described e.g. in Cariou B, Staels B. Expert Opin Investig Drugs. 2014 October; 23(10):1441-8 and is represented by the structural formula indicated below:

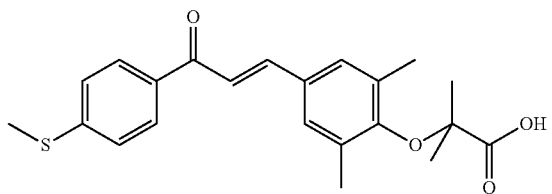 [SMILES: CSc1ccc(C(=O)/C=C/c2cc(C)c(OC(C)(C)C(=O)O)c(C)c2)cc1]

INT131 is described e.g. in. Taygerly J P, McGee L R, Rubenstein S M, Houze J B, Cushing T D, Li Y, Motani A, Chen J L, Frankmoelle W, Ye G, Learned M R, Jaen J, Miao S, Timmermans P B, Thoolen M, Kearney P, Flygare J, Beckmann H, Weiszmann J, Lindstrom M, Walker N, Liu J, Biermann D, Wang Z, Hagiwara A, Iida T, Aramaki H, Kitao Y, Shinkai H, Furukawa N, Nishiu J, Nakamura M. Bioorg Med Chem. 2013 Feb. 15; 21(4):979-92 and is represented by the structural formula indicated below:

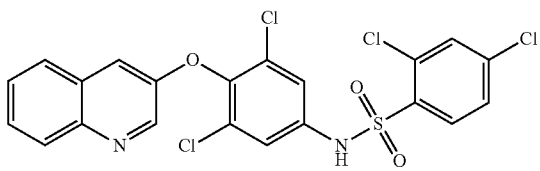 [SMILES: O=S(=O)(Nc1cc(Cl)c(Oc2cnc3ccccc3c2)c(Cl)c1)c1ccc(Cl)cc1Cl]

PPAR activation by the PPAR agonist is usually strong in the low nanomolar range to low micromolar range, e.g. in a range of 0.1 nM to 100 µM. In some embodiments the PPAR activation is weak or partial, i.e. a PPAR agonist is used in the methods of the present invention which yields maximal activation of PPAR-receptor in a reporter assay system of 10% to 100% compared to a reference PPAR agonist which is known to causes a maximum PPAR activation.

p38 Kinase Inhibitors

The term "p38 kinase inhibitor" or "p38 inhibitor" which are both used interchangeably herein refers to a drug that is inhibiting a p38 mitogen-activated protein (MAP) kinase, such as p38-alpha (MAPK14), p38-beta (MAPK11), p38-gamma (MAPK12/ERK6), and/or p38-delta (MAPK13/SAPK4). Examples of p38 inhibitors include compounds of formulae I and II and pharmaceutically acceptable salts thereof as defined herein. Further examples of p38 inhibitors include pamapimod, acumapimod, losmapimod, dilmapimod, semapimod, AZD7624, ARRY-371797, LY2228820, R9111, PH-797804, BIRB 796, VX-702, VX-745, SB 239063, SB202190, SCIO 469, BMS 582949 and pharmaceutically acceptable salts thereof.

In one embodiment, the pharmaceutical combination according to the invention comprises:
(a) a PPAR agonist;
(b) a p38 kinase inhibitor; and optionally
(c) one or more pharmaceutically acceptable diluents, excipients or carriers;
wherein said p38 inhibitor is inhibiting p38-alpha, p38-beta, p38-gamma or p38-delta or combinations thereof, preferably inhibiting p38-alpha and/or p38-beta, more preferably inhibiting p38-alpha.

In a further embodiment, the p38 inhibitor for use in a pharmaceutical combination according to the invention is a compound of formula I or II

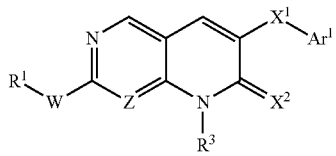

Formula I

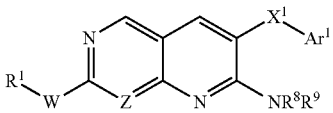

Formula II or a pharmaceutically acceptable salt thereof, wherein
Z is N or CH;
W is $NR^2$;
$X^1$ is O, $NR^4$ (where $R^4$ is hydrogen or alkyl), S, or $CR^5R^6$ (where $R^5$ and $R^6$ are independently hydrogen or alkyl) or C=O;
$X^2$ is O or $NR^7$;
$Ar^1$ is aryl or heteroaryl;
$R^2$ is hydrogen, alkyl, acyl, alkoxycarbonyl, aryloxycarbonyl, heteroalkylcarbonyl, heteroalkyloxycarbonyl or —$R^{21}$—$R^{22}$ where $R^{21}$ is alkylene or —C(=O)— and $R^{22}$ is alkyl or alkoxy;
$R^1$ is hydrogen, alkyl, haloalkyl, aryl, aralkyl, heteroaryl, heteroaralkyl, cycloalkyl, cycloalkylalkyl, heteroalkyl-substituted cycloalkyl, heterosubstituted cycloalkyl, heteroalkyl, cyanoalkyl, heterocyclyl, heterocyclylalkyl, $R^{12}$—$SO_2$-heterocycloamino (where $R^{12}$ is haloalkyl, aryl, aralkyl, heteroaryl or heteroaralkyl), —$Y^1$—C(O)—$Y^2$—$R^{11}$ (where $Y^1$ and $Y^2$ are independently either absent or an alkylene group and $R^{11}$ is hydrogen, alkyl, haloalkyl, hydroxy, alkoxy, amino, monoalkylamino or dialkylamino), (heterocyclyl)(cycloalkyl)alkyl or (heterocyclyl)(heteroaryl)alkyl;

$R^3$ is hydrogen, alkyl, cycloalkyl, cycloalkylalkyl, aryl, aralkyl, haloalkyl, heteroalkyl, cyanoalkyl, alkylene-C(O)—$R^{31}$ (where $R^{31}$ is hydrogen, alkyl, hydroxy, alkoxy, amino, monoalkylamino or dialkylamino), amino, monoalkylamino, dialkylamino or $NR^{32}$—$Y^3$—$R^{33}$ (where $Y^3$ is —C(O), —C(O)O—, —C(O)$NR^{34}$, $S(O)_2$ or $S(O)_2NR^{35}$; $R^{32}$, $R^{34}$ and $R^{35}$ are independently hydrogen or alkyl; and $R^{33}$ is hydrogen, alkyl, cycloalkyl, cycloalkylalkyl, heteroalkyl or optionally substituted phenyl) or acyl;

$R^7$ is hydrogen or alkyl; and $R^8$ and $R^9$ are independently hydrogen, alkyl, aryl, aralkyl, cycloalkyl, cycloalkylalkyl, heteroalkyl, alkylsulfonyl, arylsulfonyl, —C(O)—$R^{81}$ (where $R^{81}$ is alkyl, aryl, aralkyl, cycloalkyl, cycloalkylalkyl, heteroalkyl, alkoxy, aryloxy, amino, mono- or dialkylamino, arylamino or aryl(alkyl)amino) or $R^8$ and $R^9$ together form =$CR^{82}R^{83}$ (where $R^{82}$ and $R^{83}$ are independently hydrogen, alkyl, cycloalkyl, cycloalkylalkyl or optionally substituted phenyl) and optionally one or more pharmaceutically acceptable diluents, excipients or carriers.

In a preferred embodiment, the p38 inhibitor for use in a pharmaceutical combination according to the invention is a compound of formula I

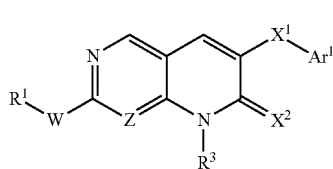

Formula I or a pharmaceutically acceptable salt thereof, wherein
Z is N or CH;
W is $NR^2$;
$X^1$ is O, $NR^4$ (where $R^4$ is hydrogen or alkyl), S, or $CR^5R^6$ (where $R^5$ and $R^6$ are independently hydrogen or alkyl) or C=O;
$X^2$ is O or $NR^7$;
$Ar^1$ is aryl or heteroaryl;
$R^2$ is hydrogen, alkyl, acyl, alkoxycarbonyl, aryloxycarbonyl, heteroalkylcarbonyl, heteroalkyloxycarbonyl or —$R^{21}$—$R^{22}$ where $R^{21}$ is alkylene or —C(=O)— and $R^{22}$ is alkyl or alkoxy;
$R^1$ is hydrogen, alkyl, haloalkyl, aryl, aralkyl, heteroaryl, heteroaralkyl, cycloalkyl, cycloalkylalkyl, heteroalkylsubstituted cycloalkyl, heterosubstituted cycloalkyl, heteroalkyl, cyanoalkyl, heterocyclyl, heterocyclylalkyl, $R^{12}$—$SO_2$-heterocycloamino (where $R^{12}$ is haloalkyl, aryl, aralkyl, heteroaryl or heteroaralkyl), —$Y^1$—C(O)—$Y^2$—$R^{11}$ (where $Y^1$ and $Y^2$ are independently either absent or an alkylene group and $R^{11}$ is hydrogen, alkyl, haloalkyl, hydroxy, alkoxy, amino, monoalkylamino or dialkylamino), (heterocyclyl)(cycloalkyl)alkyl or (heterocyclyl)(heteroaryl)alkyl;
$R^3$ is hydrogen, alkyl, cycloalkyl, cycloalkylalkyl, aryl, aralkyl, haloalkyl, heteroalkyl, cyanoalkyl, alkylene-C(O)—$R^{31}$ (where $R^{31}$ is hydrogen, alkyl, hydroxy, alkoxy, amino, monoalkylamino or dialkylamino), amino, monoalkylamino, dialkylamino or $NR^{32}$—$Y^3$—$R^{33}$ (where $Y^3$ is —C(O), —C(O)O—, —C(O)$NR^{34}$, $S(O)_2$ or $S(O)_2NR^{35}$; $R^{32}$, $R^{34}$ and $R^{35}$ are independently hydrogen or alkyl; and $R^{33}$ is hydrogen, alkyl, cycloalkyl, cycloalkylalkyl, heteroalkyl or optionally substituted phenyl) or acyl; and $R^7$ is hydrogen or alkyl and optionally one or more pharmaceutically acceptable diluents, excipients or carriers.

In a further embodiment, the p38 inhibitor for use in a pharmaceutical combination according to the invention is a compound of formula I wherein $X^1$ is $NR^4$ and $X^2$ is $NR^7$ or $X^1$ and $X^2$ are each O, wherein $R^4$ and $R^7$ are as defined above.

In a further embodiment, the p38 inhibitor for use in a pharmaceutical combination according to the invention is a compound of formula I wherein $X^1$ is $NR^4$ or O and $X^2$ is $NR^7$ or O, wherein $R^4$ and $R^7$ are as defined above.

In a further embodiment, the p38 inhibitor for use in a pharmaceutical combination according to the invention is a compound of formula I wherein W is $NR^2$ and wherein $R^2$ is hydrogen, alkyl, heteroalkyl, acyl or alkoxycarbonyl, preferably hydrogen or alkyl, more preferably hydrogen.

In yet a further embodiment, the p38 inhibitor for use in a pharmaceutical combination according to the invention is a compound of formula I wherein $R^1$ is hydrogen, alkyl, haloalkyl, cycloalkyl, cycloalkylalkyl, heteroalkylsubstituted cycloalkyl, heterosubstituted cycloalkyl, heteroalkyl, cyanoalkyl, heterocyclyl, heterocyclylalkyl or (heterocyclyl)(cycloalkyl)alkyl.

In a preferred embodiment, the p38 inhibitor for use in a pharmaceutical combination according to the invention is a compound of formula I wherein $R^2$ is hydrogen and $R^1$ is heteroalkyl or vice versa.

In yet a further embodiment, the p38 inhibitor for use in a pharmaceutical combination according to the invention is a compound of formula I wherein $R^1$ is hydrogen, alkyl, haloalkyl, heteroalkyl or cyanoalkyl.

In yet a further embodiment, the p38 inhibitor for use in a pharmaceutical combination according to the invention is a compound of formula I wherein $R^1$ is cycloalkyl, cycloalkylalkyl, heteroalkylsubstituted cycloalkyl, heterosubstituted cycloalkyl, heterocyclyl, heterocyclylalkyl or (heterocyclyl)(cycloalkyl)alkyl.

In a preferred embodiment, the p38 inhibitor for use in a pharmaceutical combination according to the invention is a compound of formula I wherein each of $R^1$ and $R^2$ is independently selected from hydrogen and hydroxyalkyl, preferably from hydrogen, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl, 2-(hydroxymethyl)-3-hydroxypropyl, 3-hydroxy-1-(2-hydroxyethyl)-propyl and 2-hydroxy-1-methylethyl, more preferably from hydrogen, 2-hydroxyethyl, 2,3-dihydroxypropyl and 1-(hydroxymethyl)2-hydroxyethyl, most preferably from hydrogen, 2-hydroxy-propyl, 3-hydroxy-1-(2-hydroxyethyl)-propyl and 2-hydroxy-1-methylethyl.

In yet a further embodiment, the p38 inhibitor for use in a pharmaceutical combination according to the invention is a compound of formula I wherein $R^3$ is hydrogen, alkyl, cycloalkyl, cycloalkylalkyl, haloalkyl, heteroalkyl, cyanoalkyl, alkylene-C(O)—$R^{31}$ (where $R^{31}$ is hydrogen, alkyl, hydroxy, alkoxy, amino, monoalkylamino or dialkylamino) or acyl.

In yet a further embodiment, the p38 inhibitor for use in a pharmaceutical combination according to the invention is a compound of formula I wherein $R^3$ is hydrogen, alkyl, haloalkyl, heteroalkyl, cyanoalkyl, cycloalkyl or cycloalkylalkyl.

In yet a further embodiment, the p38 inhibitor for use in a pharmaceutical combination according to the invention is a compound of formula I wherein $R^3$ is hydrogen, alkyl, haloalkyl, heteroalkyl or cyanoalkyl.

In yet a further embodiment, the p38 inhibitor for use in a pharmaceutical combination according to the invention is a compound of formula I wherein $R^3$ is cycloalkyl or cycloalkylalkyl.

In yet a further embodiment, the p38 inhibitor for use in a pharmaceutical combination according to the invention is a compound of formula I wherein $X^1$ and $X^2$ are both O.

In yet a further embodiment, the p38 inhibitor for use in a pharmaceutical combination according to the invention is a compound of formula I wherein $R^1$ is alkyl or heteroalkyl.

In yet a further embodiment, the p38 inhibitor for use in a pharmaceutical combination according to the invention is a compound of formula I wherein $R^1$ is heteroalkyl, preferably 3-hydroxy-1-(2-hydroxyethyl)-propyl or 2-hydroxy-1-methylethyl.

In yet a further embodiment, the p38 inhibitor for use in a pharmaceutical combination according to the invention is a compound of formula I wherein $R^3$ is alkyl or heteroalkyl.

In yet a further embodiment, the p38 inhibitor for use in a pharmaceutical combination according to the invention is a compound of formula I wherein $R^3$ is alkyl, preferably C1-C5 alkyl, more preferably C1-C4 alkyl, more preferably C1-C3 alkyl. In a particularly preferred embodiment, $R^3$ is ethyl or methyl, preferably methyl.

In yet a further embodiment, the p38 inhibitor for use in a pharmaceutical combination according to the invention is a compound of formula I wherein $R^3$ is heteroalkyl, preferably 2-hydroxy-propyl.

In yet a further embodiment, the p38 inhibitor for use in a pharmaceutical combination according to the invention is a compound of formula I wherein W is NH.

In yet a further embodiment, the p38 inhibitor for use in a pharmaceutical combination according to the invention is a compound of formula I wherein Z is N.

In yet a further embodiment, the p38 inhibitor for use in a pharmaceutical combination according to the invention is a compound of formula I wherein $Ar^1$ is aryl, preferably phenyl optionally substituted with one, two or three halo substituents, most preferably phenyl substituted with two halo substituents in ortho and para position. In a particularly preferred embodiment, $Ar^1$ is 2,4-difluorophenyl.

In yet a further embodiment, the p38 inhibitor for use in a pharmaceutical combination according to the invention is a compound of formula I wherein $X^1$ is $NR^4$ and $X^2$ is $NR^7$ or $X^1$ and $X^2$ are each O, wherein $R^4$ and $R^7$ are as defined above; and wherein $R^1$ is hydrogen, alkyl, haloalkyl, cycloalkyl, cycloalkylalkyl, heteroalkylsubstituted cycloalkyl, heterosubstituted cycloalkyl, heteroalkyl, cyanoalkyl, heterocyclyl, heterocyclylalkyl or (heterocyclyl)(cycloalkyl)alkyl; and wherein $R^3$ is hydrogen, alkyl, cycloalkyl, cycloalkylalkyl, haloalkyl, heteroalkyl, cyanoalkyl, alkylene-C(O)—$R^{31}$ (where $R^{31}$ is hydrogen, alkyl, hydroxy, alkoxy, amino, monoalkylamino or dialkylamino) or acyl; and wherein W is $NR^2$, wherein $R^2$ is hydrogen, alkyl, acyl or alkoxycarbonyl; and wherein $Ar^1$ is aryl; and wherein Z is N.

In a preferred embodiment, the p38 inhibitor for use in a pharmaceutical combination according to the invention is a compound of formula I wherein $X^1$ and $X^2$ are each O and wherein Z is N and wherein W is NH and wherein $Ar^1$ is phenyl optionally substituted by one, two or three halo substituents and wherein $R^1$ is heteroalkyl and wherein $R^3$ is alkyl or heteroalkyl.

In a further embodiment, the p38 inhibitor for use in a pharmaceutical combination according to the invention is a compound of formula II

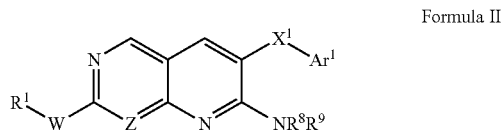

Formula II or a pharmaceutically acceptable salt thereof, wherein $Ar^1$, W, $X^1$, Z, $R^1$, $R^8$ and $R^9$ are as defined in any of the embodiments above.

Unless otherwise stated, the following terms have the meanings given below:

"Acyl" means a radical —C(O)R, where R is hydrogen, alkyl, cycloalkyl, cycloalkylalkyl, phenyl or phenylalkyl wherein alkyl, cycloalkyl, cycloalkylalkyl, and phenylalkyl are as defined herein. Representative examples include, but are not limited to formyl, acetyl, cylcohexylcarbonyl, cyclohexylmethylcarbonyl, benzoyl, benzylcarbonyl, and the like.

"Acylamino" means a radical-NR'C(O)R, where R' is hydrogen or alkyl, and R is hydrogen, alkyl, cycloalkyl, cycloalkylalkyl, phenyl or phenylalkyl wherein alkyl, cycloalkyl, cycloalkylalkyl, and phenylalkyl are as defined herein. Representative examples include, but are not limited to formylamino, acetylamino, cylcohexylcarbonylamino, cyclohexylmethyl-carbonylamino, benzoylamino, benzylcarbonylamino, and the like.

"Alkoxy" means a radical —OR where R is an alkyl as defined herein. Examples are methoxy, ethoxy, propoxy, butoxy and the like.

"Alkoxycarbonyl" means a radical R—O—C(O)—, wherein R is an alkyl as defined herein.

"Alkyl" means a linear saturated monovalent hydrocarbon radical of one to six carbon atoms or a branched saturated monovalent hydrocarbon radical of three to six carbon atoms. Examples include methyl, ethyl, propyl, 2-propyl, n-butyl, iso-butyl, tert-butyl, pentyl, and the like. Preferred are C1-C3 alkyl groups, in particular ethyl and methyl.

"Alkylsulfonyl" means a radical R—S(O)$_2$—, wherein R is alkyl as defined herein.

"Alkylene" means a linear saturated divalent hydrocarbon radical of one to six carbon atoms or a branched saturated divalent hydrocarbon radical of three to six carbon atoms. Examples are methylene, ethylene, 2,2-dimethylethylene, propylene, 2-methylpropylene, butylen, pentylene, and the like.

"Aryl" means a monovalent monocyclic or bicyclic aromatic hydrocarbon radical which is optionally substituted independently with one or more substituents, preferably one, two or three substituents preferably selected from the group consisting of alkyl, hydroxy, alkoxy, haloalkyl, haloalkoxy, Y—C(O)—R (where Y is absent or an alkylene group and R is hydrogen, alkyl, haloalkyl, haloalkoxy, hydroxy, alkoxy, amino, monoalkylamino or dialkylamino), heteroalkyl, heteroalkyloxy, heteroalkylamino, halo, nitro, cyano, amino, monoalkylamino, dialkylamino, alkylsulfonylamino, heteroalkylsulfonylamino, sulfonamido, methylenedioxy, ethylenedioxy, heterocyclyl or heterocyclylalkyl. Monocyclic aryl groups, optionally substituted as described above, are preferred. More specifically, the term aryl includes, but is not limited to, phenyl optionally substituted independently with one, two or three substituents preferably selected from the group consisting of alkyl, hydroxy, alkoxy, haloalkyl, haloalkoxy, Y—C(O)—R (where Y is absent or an alkylene group and R is hydrogen, alkyl, haloalkyl, haloalkoxy, hydroxy, alkoxy, amino, monoalkylamino or dialkylamino), heteroalkyl, heteroalkyloxy, heteroalkylamino, halo, nitro, cyano, amino, monoalkylamino, dialkylamino, alkylsulfonylamino, heteroalkylsulfonylamino, sulfonamido, methylenedioxy, ethylenedioxy, heterocyclyl and heterocyclylalkyl. Particularly preferred aryl groups are substituted phenyl groups selected from the group consisting of chlorophenyl, methoxyphenyl, 2-fluorophenyl, 2,4-difluorophenyl, 1-naphthyl and 2-naphthyl.

"Arylsulfonyl" means a radical R—S(O)$_2$—, wherein R is aryl as defined herein.

"Aralkyl" refers to an aryl group as defined herein bonded directly through an alkylene group, e.g. benzyl.

"Aryloxy" means a radical —OR where R is an aryl as defined herein, e.g. phenoxy.

"Aryloxycarbonyl" means a radical R—C(=O)— where R is aryloxy, e.g. phenoxycarbonyl.

"Cycloalkyl" refers to a saturated monovalent cyclic hydrocarbon radical of three to seven ring carbons or more specifically those of the specific compounds listed in the enclosed tables or being described in the examples. It is understand that these radicals can be grouped also in a group covering only such radicals but of the first or the second priority application or of both priority applications e.g., cyclopropyl, cyclobutyl, cyclohexyl, 4-methyl-cyclohexyl, and the like.

"Cycloalkylalkyl" means a radical —R$^a$R$^b$ where R$^a$ is an alkylene group and R$^b$ is cycloalkyl group as defined herein, e.g., cyclohexylmethyl, and the like.

"Substituted cycloalkyl" means a cycloalkyl radical as defined herein with one, two or three (preferably one) ring hydrogen atoms independently replaced by cyano or —Y—C(O)R (where Y is absent or an alkylene group and R is hydrogen, alkyl, haloalkyl, hydroxy, alkoxy, amino, monoalkylamino, dialkylamino, or optionally substituted phenyl) or more specifically those of the specific compounds listed in the enclosed tables or being described in the examples.

"Halo" means fluoro, chloro, bromo, or iodo, preferably fluoro and chloro.

"Haloalkyl" means alkyl substituted with one or more same or different halo atoms, e.g. —CH$_2$Cl, —CF$_3$, —CH$_2$CF$_3$, —CH$_2$CCl$_3$, and the like.

"Heteroalkyl" means an alkyl radical as defined herein wherein one, two or three hydrogen atoms have been replaced with a substituent independently selected from the group consisting of —OR$^a$, —N(O)$_n$R$^b$R$^c$ (where n is 0 or 1 if R$^b$ and R$^c$ are both independently alkyl, cycloalkyl or cycloalkylalkyl, and 0 if not) and —S(O)$_n$R$^d$ (where n is an integer from 0 to 2), with the understanding that the point of attachment of the heteroalkyl radical is through a carbon atom, wherein R$^a$ is hydrogen, acyl, alkoxycarbonyl, alkyl, cycloalkyl, or cycloalkylalkyl; R$^b$ and R$^c$ are independently of each other hydrogen, acyl, alkoxycarbonyl, alkyl, cycloalkyl, cycloalkylalkyl, alkylsulfonyl, aminosulfonyl, mono- or dialkylaminosulfonyl, aminoalkyl, mono- or di-alkylaminoalkyl, hydroxyalkyl, alkoxyalkyl, hydroxyalkylsulfonyl or alkoxyalkylsulfonyl; and when n is 0, R$^d$ is hydrogen, alkyl, cycloalkyl, cycloalkylalkyl or optionally substituted phenyl, and when n is 1 or 2, R$^d$ is alkyl, cycloalkyl, cycloalkylalkyl, optionally substituted phenyl, amino, acylamino, monoalkylamino, or dialkylamino. Preferred heteroalkyl groups include hydroxyalkyl groups, preferably C1-C6 hydroxyalkyl groups. Representative examples include, but are not limited to, 2-hydroxyethyl, 2-hydroxy-propyl, 3-hydroxypropyl, 2-hydroxy-1-hydroxymethylethyl, 2-hydroxy-1-methylethyl, 2,3-dihydroxypropyl, 1-hydroxymethylethyl, 3-hydroxybutyl, 2,3-dihydroxybutyl, 2-hydroxy-1-methylpropyl, 3-hydroxy-1-(2-hydroxyethyl)-propyl, 2-aminoethyl, 3-aminopropyl, 2-methylsulfonylethyl, aminosulfonylmethyl, aminosulfonylethyl, aminosulfonylpropyl, methylaminosulfonylmethyl, methylaminosulfonylethyl, methylaminosulfonylpropyl, and the like. Particularly preferred heteroalkyl groups are 2-hydroxy-propyl, 3-hydroxy-1-(2-hydroxyethyl)-propyl or 2-hydroxy-1-methylethyl.

"Hydroxyalkyl" means an alkyl radical as defined herein, substituted with one or more, preferably one, two or three hydroxy groups, provided that the same carbon atom does not carry more than one hydroxy group. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl, 2-(hydroxymethyl)-3-hydroxypropyl, 3-hydroxy-1-(2-hydroxyethyl)-propyl and 2-hydroxy-1-methylethyl, preferably 2-hydroxyethyl, 2,3-dihydroxypropyl and 1-(hydroxymethyl)2-hydroxyethyl, more preferably 2-hydroxy-propyl, 3-hydroxy-1-(2-hydroxyethyl)-propyl and 2-hydroxy-1-methylethyl. Accordingly, as used herein, the term "hydroxyalkyl" is used to define a subset of heteroalkyl groups.

"Heteroalkylcarbonyl" means the group R$^a$—C(=O)—, where R$^a$ is a heteroalkyl group. Representative examples include acetyloxymethylcarbonyl, aminomethylcarbonyl, 4-acetyloxy-2,2-dimethyl-butan-2-oyl, 2-amino-4-methyl-pentan-2-oyl, and the like.

"Heteroalkyloxy" means the group R$^a$—O—, where R$^a$ is a heteroalkyl group. Representative examples include (Me-C(=O)—O—CH$_2$—O—, and the like.

"Heteroalkyloxycarbonyl" means the group R$^a$—C(=O), where R$^a$ is heteroalkyloxy. Representative examples include 1-acetyloxy-methoxycarbonyl (Me-C(=O)—OCH$_2$—O—C(=O)—) and the like.

"Heteroaryl" means a monovalent monocyclic or bicyclic radical of 5 to 12 ring atoms having at least one aromatic ring containing one, two, or three ring heteroatoms selected from the group consisting of N, O, or S, the remaining ring atoms being C, with the understanding that the attachment point of the heteroaryl radical will be on an aromatic ring. The heteroaryl ring is optionally substituted independently with one or more substituents, preferably one or two substituents, selected from the group consisting of alkyl, haloalkyl, heteroalkyl, hydroxy, alkoxy, halo, nitro or cyano. More specifically the term heteroaryl includes, but is not limited to, pyridyl, furanyl, thienyl, thiazolyl, isothiazolyl, triazolyl, imidazolyl, isoxazolyl, pyrrolyl, pyrazolyl, pyrimidinyl, benzofuranyl, tetrahydrobenzofuranyl, isobenzofuranyl, benzothiazolyl, benzoisothiazolyl, benzotriazolyl, indolyl, isoindolyl, benzoxazolyl, quinolyl, tetrahydroquinolinyl, isoquinolyl, benzimidazolyl, benzisoxazolyl or benzothienyl, imidazo[1,2-a]-pyridinyl, imidazo[2,1-b]thiazolyl, and derivatives thereof.

"Heteroaralkyl" means a radical —R$^a$R$^b$ where R$^a$ is an alkylene group and R$^b$ is a heteroaryl group, e.g. pyridin-3-ylmethyl, imidazolylethyl, pyridinylethyl, 3-(benzofuran-2-yl)propyl, and the like.

"Heteroalkylsubstituted cycloalkyl" means a cycloalkyl radical as defined herein wherein one, two or three hydrogen atoms in the cycloalkyl radical have been replaced with a heteroalkyl group with the understanding that the heteroalkyl radical is attached to the cycloalkyl radical via a carbon-carbon bond. Representative examples include, but are not limited to, 1-hydroxymethylcyclopentyl, 2-hydroxymethyl-cyclohexyl, and the like.

"Heterosubstituted cycloalkyl" means a cycloalkyl radical as defined herein wherein one, two or three hydrogen atoms in the cycloalkyl radical have been replaced with a substituent independently selected from the group consisting of hydroxy, alkoxy, amino, acylamino, monoalkylamino, dialkylamino, oxo(C=O), imino, hydroximino (=NOH), NR'SO$_2$R$^d$ (where R' is hydrogen or alkyl and R$^d$ is alkyl, cycloalkyl, hydroxyalkyl, amino, monoalkylamino or dialkylamino), —X—Y—C(O)R (where X is O or NR', Y is alkylene or absent, R is hydrogen, alkyl, haloalkyl, alkoxy, amino, monoalkylamino, dialkylamino, or optionally substituted phenyl, and R' is H or alkyl), or —S(O)$_n$R (where n is an integer from 0 to 2) such that when n is 0, R is hydrogen, alkyl, cycloalkyl, cycloalkylalkyl optionally substituted phenyl or thienyl, and when n is 1 or 2, R is alkyl, cycloalkyl, cycloalkylalkyl, optionally substituted phenyl, thienyl, amino, acylamino, monoalkylamino or dialkylamino. Representative examples include, but are not limited to, 2-, 3-, or 4-hydroxycyclohexyl, 2-, 3-, or 4-aminocyclohexyl, 2-, 3-, or 4-methanesulfonamido-cyclohexyl, and the like, preferably 4-hydroxycyclohexyl, 2-aminocyclohexyl or 4-methanesulfonamido-cyclohexyl.

"Heterosubstituted cycloalkyl-alkyl" means a radical R$^a$R$^b$— where R$^a$ is a heterosubstituted cycloalkyl radical and R$^b$ is an alkylene radical.

"Heterocycloamino" means a saturated monovalent cyclic group of 4 to 8 ring atoms, wherein one ring atom is N and the remaining ring atoms are C. Representative examples include piperidine and pyrrolidine.

"Heterocyclyl" means a saturated or unsaturated non-aromatic cyclic radical of 3 to 8 ring atoms in which one or two ring atoms are heteroatoms selected from N, O, or S(O)$_n$ (where n is an integer from 0 to 2), the remaining ring atoms being C, where one or two C atoms may optionally be replaced by a carbonyl group. The heterocyclyl ring may be optionally substituted independently with one, two, or three substituents selected from the group consisting of alkyl, haloalkyl, heteroalkyl, halo, nitro, cyano, cyanoalkyl, hydroxy, alkoxy, amino, monoalkylamino, dialkylamino, aralkyl, —(X)$_n$—C(O)R (where X is O or NR', n is 0 or 1, R is hydrogen, alkyl, haloalkyl, hydroxy (when n is 0), alkoxy, amino, monoalkylamino, dialkylamino, or optionally substituted phenyl, and R' is H or alkyl), -alkylene-C(O)R$^a$ (where R$^a$ is alkyl, OR or NR'R" and R is hydrogen, alkyl or haloalkyl, and R' and R" are independently hydrogen or alkyl), or —S(O)$_n$R (where n is an integer from 0 to 2) such that when n is 0, R is hydrogen, alkyl, cycloalkyl, or cycloalkylalkyl, and when n is 1 or 2, R is alkyl, cycloalkyl, cycloalkylalkyl, amino, acylamino, monoalkylamino, dialkylamino or heteroalkyl. More specifically the term heterocyclyl includes, but is not limited to, tetrahydropyranyl, piperidino, N-methylpiperidin-3-yl, piperazino, N-methylpyrrolidin-3-yl, 3-pyrrolidino, morpholino, thiomorpholino, thiomorpholino-1-oxide, thiomorpholino-1,1-dioxide, 4-(1,1-dioxo-tetrahydro-2H-thiopyranyl), pyrrolinyl, imidazolinyl, N-methanesulfonyl-piperidin-4-yl, and the derivatives thereof.

"Heterocyclylalkyl" means a radical —R$^a$R$^b$ where R$^a$ is an alkylene group and R$^b$ is a heterocyclyl group as defined above, e.g. tetrahydropyran-2-ylmethyl, 2- or 3-piperidinyl-methyl, 3-(4-methyl-piperazin-1-yl)propyl and the like.

"(Heterocyclyl)(cycloalkyl)alkyl" means an alkyl radical wherein two hydrogen atoms have been replaced with a heterocyclyl group and a cycloalkyl group.

"(Heterocyclyl)(heteroaryl)alkyl" means an alkyl radical wherein two hydrogen atoms have been replaced with a heterocycyl group and a heteroaryl group.

"Amino" means a radical —NH$_2$.

"Monoalkylamino" means a radical —NHR where R is an alkyl, hydroxyalkyl, cycloalkyl, or cycloalkylalkyl group as defined above, e.g. methylamino, (1-methylethyl) amino, hydroxymethylamino, cyclohexylamino, cyclohexylmethyl-amino, cyclohexylethylamino, and the like.

"Dialkylamino" means a radical —NRR' where R and R' independently represent an alkyl, hydroxyalkyl, cycloalkyl, or cycloalkylalkyl group as defined herein. Representative examples include, but are not limited to dimethylamino, methylethylamino, di(1-methylethyl)amino, (methyl)(hydroxymethyl)amino, (cyclohexyl)(methyl)amino, (cyclohexyl)(ethyl)amino, (cyclohexyl)(propyl)amino, (cyclohexylmethyl)(methyl)amino, (cyclohexylmethyl)(ethyl)amino, and the like.

"Optionally substituted phenyl" means a phenyl ring which is optionally substituted independently with one or more substituents, preferably one, two or three substituents, more preferably two substituents selected from the group consisting of alkyl, hydroxy, alkoxy, haloalkyl, haloalkoxy, heteroalkyl, halo, nitro, cyano, amino, methylenedioxy, ethylenedioxy, and acyl, preferably halo, most preferably fluoro.

Thus, in a preferred embodiment, the p38 inhibitor for use in a pharmaceutical combination according to the invention is selected from the group consisting of pamapimod, acumapimod, losmapimod, dilmapimod, semapimod, AZD7624, ARRY-371797, LY2228820, R9111, PH-797804, BIRB 796, VX-702, VX-745, SB 239063, SB202190, SCIO 469, and BMS 582949 and a pharmaceutically acceptable salt thereof. More preferred is a p38 inhibitor for use in a pharmaceutical combination according to the invention selected from the group consisting of pamapimod, losmapimod, LY2228820, BMS 582949 or pharmaceutically acceptable salts and mixtures thereof, even more preferably pamapimod or a pharmaceutically acceptable salt thereof.

In a particularly preferred embodiment, the p38 inhibitor is pamapimod, having the chemical name 6-(2,4-Difluoro-phenoxy)-2-[3-hydroxy-1-(2-hydroxyethyl)-propylamino]-8-methyl-8H-pyrido[2,3-d]pyrimidin-7-one and the chemical formula III or a pharmaceutically acceptable salt thereof.

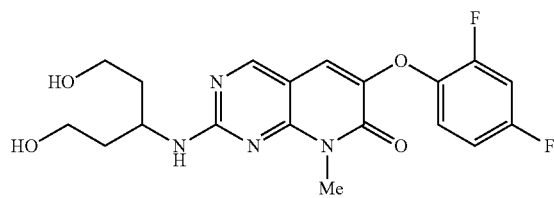

Formula III

Pamapimod and its synthesis are described e.g. in WO2008/151992 and in WO2002/064594 and in e.g. Hill R J, Dabbagh K, Phippard D, Li C, Suttmann R T, Welch M, Papp E, Song K W, Chang K C, Leaffer D, Kim Y-N, Roberts R T, Zabka T S, Aud D, Dal Porto J, Manning A M, Peng S L, Goldstein D M, and Wong B R; Pamapimod, a Novel p38 Mitogen-Activated Protein Kinase Inhibitor: Preclinical Analysis of Efficacy and Selectivity J Pharmacol Exp Ther. December 2008 327:610-619.

A further particularly preferred p38 inhibitor is losmapimod, having the chemical name 6-(5-((cyclopropylamino) carbonyl)-3-fluoro-2-methylphenyl)-N-(2,2-dimethylpropyl)-3-pyridinecarboxamide and the chemical formula IV or a pharmaceutically acceptable salt thereof.

Formula IV

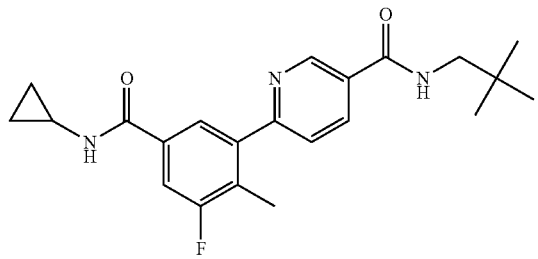

Losmapimod is described in e.g. Cheriyan J, Webb A J, Sarov-Blat L, Elkhawad M, Wallace S M, Mäki-Petäjä K M, Collier D J, Morgan J, Fang Z, Willette R N, Lepore J J, Cockcroft J R, Sprecher D L, Wilkinson I B. Inhibition of p38 mitogen-activated protein kinase improves nitric oxide-mediated vasodilatation and reduces inflammation in hypercholesterolemia. Circulation, 2011 Feb. 8; 123(5):515-23.

Yet a further particularly preferred p38 inhibitor is LY2228820, having the chemical name 3-(2,2-Dimethylpropyl)-5-[4-(4-fluorophenyl)-2-(2-methyl-2-propanyl)-1H-imidazol-5-yl]-3H-imidazo[4,5-b]pyridin-2-amine and the chemical formula V or a pharmaceutically acceptable salt thereof.

Formula V

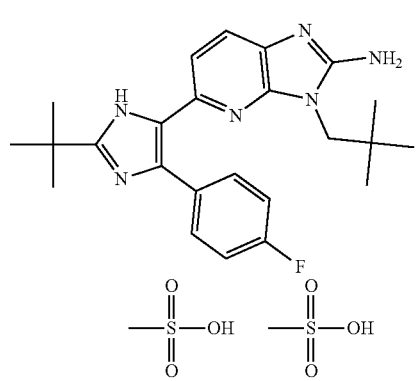

LY2228820 is described in e.g. Campbell R M, Anderson B D, Brooks N A, Brooks H B, Chan E M, De Dios A, Gilmour R, Graff J R, Jambrina E, Mader M, McCann D, Na S, Parsons S H, Pratt S E, Shih C, Stancato L F, Starling J J, Tate C, Velasco J A, Wang Y, Ye X S. Characterization of LY2228820 dimesylate, a potent and selective inhibitor of p38 MAPK with antitumor activity. Mol Cancer Ther. 2014 February; 13(2):364-74.

Yet a further particularly preferred p38 inhibitor is BMS 582949, having the chemical name 4-(5-(cyclopropylcarbamoyl)-2-methylphenylamino)-5-methyl-N-propylpyrrolo[1,2-f][1,2,4]triazine-6-carboxamide and the chemical formula VI or a pharmaceutically acceptable salt thereof.

Formula VI

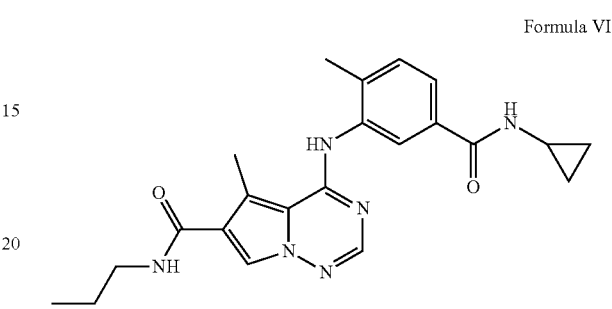

BMS 582949 is described in e.g. Liu C, Lin J, Wrobleski S T, Lin S, Hynes J, Wu H, Dyckman A J, Li T, Wityak J, Gillooly K M, Pitt S, Shen D R, Zhang R F, McIntyre K W, Salter-Cid L, Shuster D J, Zhang H, Marathe P H, Doweyko A M, Sack J S, Kiefer S E, Kish K F, Newitt J A, McKinnon M, Dodd J H, Barrish J C, Schieven G L, Leftheris K. Discovery of 4-(5-(cyclopropylcarbamoyl)-2-methylphenylamino)-5-methyl-N-propylpyrrolo[1,2-f][1,2,4]triazine-6-carboxamide (BMS-582949), a clinical p38-alpha MAP kinase inhibitor for the treatment of inflammatory diseases. J Med Chem. 2010 Sep. 23; 53(18):6629-39.

Acumapimod has the chemical name 3-[5-Amino-4-(3-cyanobenzoyl)-1H-pyrazol-1-yl]-N-cyclopropyl-4-methyl-benzamide and is described in e.g. De Buck S, Hueber W, Vitaliti A, Straube F, Emotte C, Bruin G, Woessner R. Population PK-PD Model for Tolerance Evaluation to the p38 MAP Kinase Inhibitor BCT197. CPT Pharmacometrics Syst Pharmacol. 2015 December; 4(12):691-700, and is represented by the structural formula indicated below:

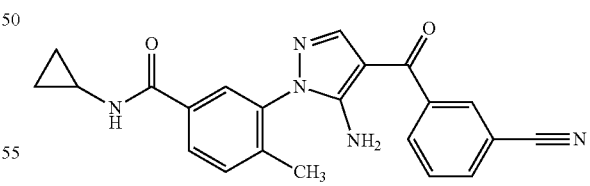

Dilmapimod is described in e.g. Christie J D, Vaslef S, Chang P K, May A K, Gunn S R, Yang S, Hardes K, Kahl L, Powley W M, Lipson D A, Bayliffe A I, Lazaar A L. A Randomized Dose-Escalation Study of the Safety and Anti-Inflammatory Activity of the p38 Mitogen-Activated Protein Kinase Inhibitor Dilmapimod in Severe Trauma Subjects at Risk for Acute Respiratory Distress Syndrome. Crit Care Med. 2015 September; 43(9):1859-69, and is represented by the structural formula indicated below:

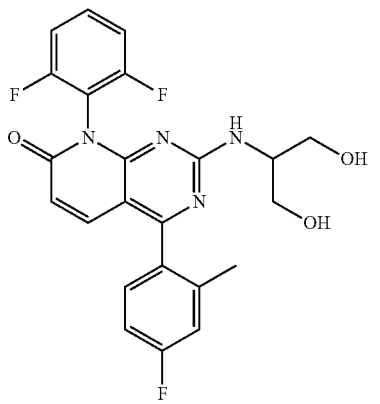 [SMILES: Cc1cc(F)ccc1-c1nc(NC(CO)CO)nc2c1ccc(=O)n2-c1c(F)cccc1F]

Semapimod is described in e.g. Bianchi, M.; Ulrich, P.; Bloom, O.; Meistrell m, M., I. I.; Zimmerman, G. A.; Schmidtmayerova, H.; Bukrinsky, M.; Donnelley, T.; Bucala, R.; Sherry, B.; Manogue, K. R.; Tortolani, A. J.; Cerami, A.; Tracey, K. J. (March 1995). Molecular Medicine (Cambridge, Mass.). 1 (3): 254-266 or in e.g. Wang J, Grishin A V, Ford H R. Experimental Anti-Inflammatory Drug Semapimod Inhibits TLR Signaling by Targeting the TLR Chaperone gp96. J Immunol. 2016 Jun. 15; 196(12): 5130-7 and is represented by the structural formula as indicated below:

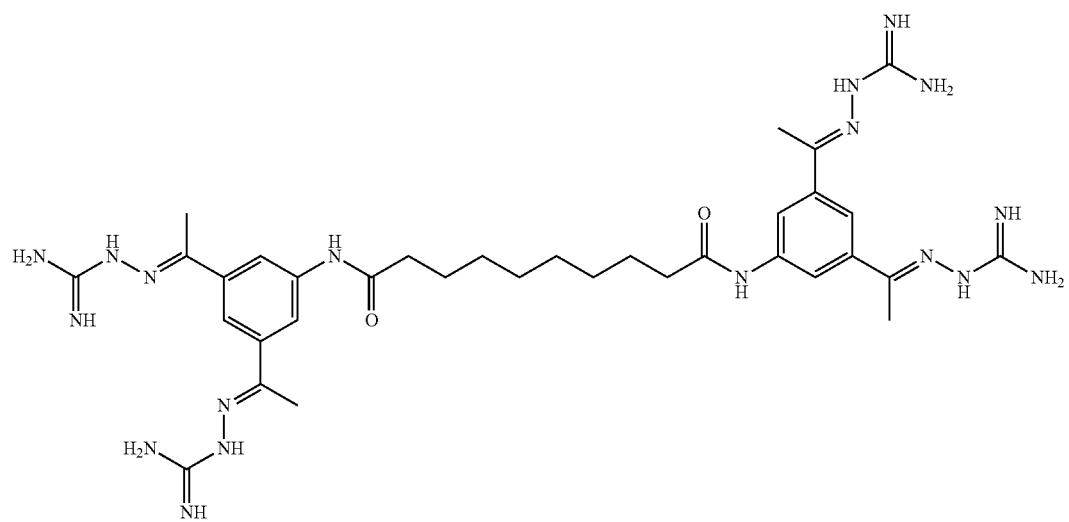 [SMILES: C/C(=N\NC(=N)N)c1cc(NC(=O)CCCCCCCCC(=O)Nc2cc(/C(C)=N/NC(=N)N)cc(/C(C)=N/NC(=N)N)c2)cc(/C(C)=N/NC(=N)N)c1]

AZD7624 is described in e.g. Patel N, Cunoosamy D, Hegelund-Myrback T, Pehrson R, Taib Z, Jansson P, Lundin S, Greenaway S, Clarke G, Siew L. AZD7624, an inhaled p38 inhibitor for COPD, attenuates lung and systemic inflammation after LPS Challenge in humans. Eur Resp J. DOI: 10.1183/13993003.1 September 2015, and is represented by the structural formula as indicated below:

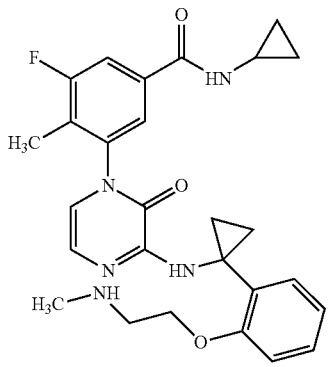 [SMILES: CNCCOc1ccccc1C1(Nc2nccn(-c3cc(C(=O)NC4CC4)cc(F)c3C)c2=O)CC1]

ARRY-371797 is described in e.g. Muchir A, Wu W, Choi J C, Iwata S, Morrow J, Homma S, Worman H J. Abnormal p38-alpha mitogen-activated protein kinase signaling in dilated cardiomyopathy caused by lamin A/C gene mutation. Hum Mol Genet. 2012 Oct. 1; 21(19):4325-33, and is represented by the structural formula as indicated below:

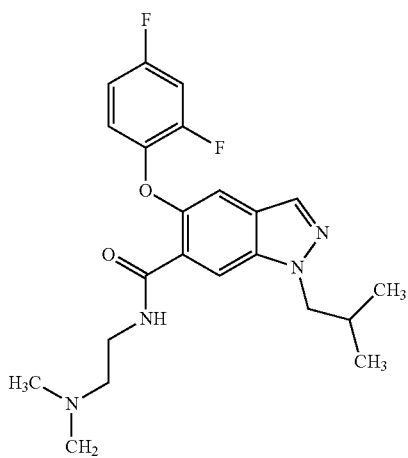 [SMILES: CC(C)Cn1ncc2cc(Oc3ccc(F)cc3F)c(C(=O)NCCN(C)C)cc21]

R9111 and its synthesis is described in WO2005/047284 and in e.g. Hill R J, Dabbagh K, Phippard D, Li C, Suttmann R T, Welch M, Papp E, Song K W, Chang K C, Leaffer D, Kim Y-N, Roberts R T, Zabka T S, Aud D, Dal Porto J, Manning A M, Peng S L, Goldstein D M, and Wong B R; Pamapimod, a Novel p38 Mitogen-Activated Protein Kinase Inhibitor: Preclinical Analysis of Efficacy and Selectivity J Pharmacol Exp Ther. December 2008 327:610-619 and is represented by the structural formula as indicated below:

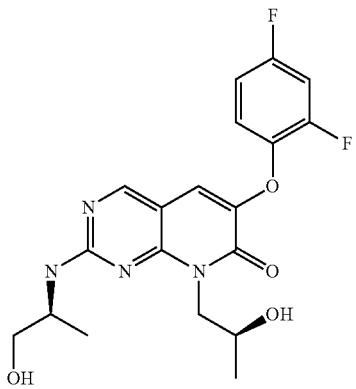 [SMILES: C[C@H](O)Cn1c(=O)c(Oc2ccc(F)cc2F)cc2cnc(N[C@@H](C)CO)nc21]

PH-797804 is described in e.g. Xing L, Devadas B, Devraj R V, Selness S R, Shieh H, Walker J K, Mao M, Messing D, Samas B, Yang J Z, Anderson G D, Webb E G, Monahan J B. Discovery and characterization of atropisomer PH-797804, a p38 MAP kinase inhibitor, as a clinical drug candidate. ChemMedChem. 2012 Feb. 6; 7(2):273-80, and is represented by the structural formula indicated below:

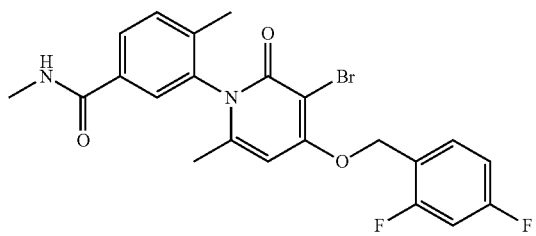 [SMILES: CNC(=O)c1ccc(C)c(-n2c(C)cc(OCc3ccc(F)cc3F)c(Br)c2=O)c1]

BIRB 796 is described in e.g. Dietrich J, Hulme C, Hurley L H. The design, synthesis, and evaluation of 8 hybrid DFG-out allosteric kinase inhibitors: a structural analysis of the binding interactions of Gleevec, Nexavar, and BIRB-796. Bioorg Med Chem. 2010 Aug. 1; 18(15):5738-48, and is represented by the structural formula indicated below:

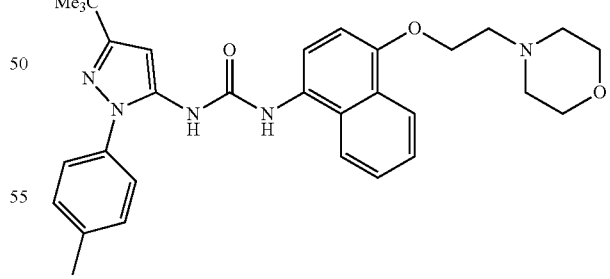

VX-702 is described in e.g. Damjanov N, Kauffman R S, Spencer-Green G T.

Efficacy, pharmacodynamics, and safety of VX-702, a novel p38 MAPK inhibitor, in rheumatoid arthritis: results of two randomized, double-blind, placebo-controlled clinical studies. Arthritis Rheum. 2009 May; 60(5):1232-41, and is represented by the structural formula indicated below:

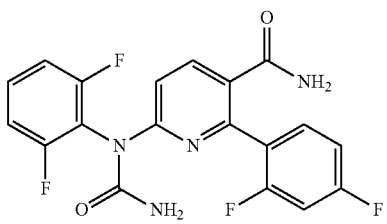 [SMILES: NC(=O)c1ccc(N(C(N)=O)c2c(F)cccc2F)nc1-c1ccc(F)cc1F]

VX-745 is described in e.g. Duffy J P, Harrington E M, Salituro F G, Cochran J E, Green J, Gao H, Bemis G W, Evindar G, Galullo V P, Ford P J, Germann U A, Wilson K P, Bellon S F, Chen G, Taslimi P, Jones P, Huang C, Pazhanisamy S, Wang Y M, Murcko M A, Su M S. The Discovery of VX-745: A Novel and Selective p38-alpha Kinase Inhibitor. ACS Med Chem Lett. 2011 Jul. 28; 2(10): 758-63, and is represented by the structural formula indicated below:

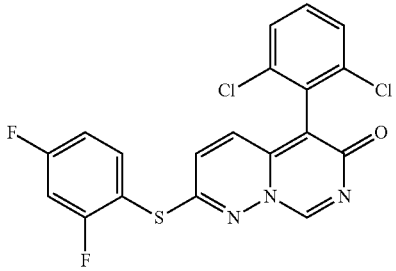 [SMILES: O=c1ncn2nc(Sc3ccc(F)cc3F)ccc2c1-c1c(Cl)cccc1Cl]

SB239063 is described in e.g. Strassburger M, Braun H, Reymann K G. Anti-inflammatory treatment with the p38 mitogen-activated protein kinase inhibitor SB239063 is neuroprotective, decreases the number of activated microglia and facilitates neurogenesis in oxygen-glucose-deprived hippocampal slice cultures. Eur J Pharmacol. 2008 Sep. 11; 592(1-3):55-61, and is represented by the structural formula indicated below:

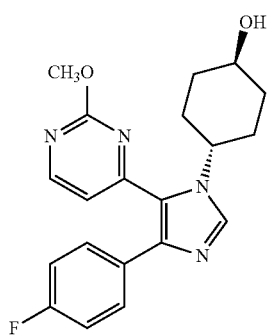

SB202190 is described in e.g. Hirosawa M, Nakahara M, Otosaka R, Imoto A, Okazaki T, Takahashi S. The p38 pathway inhibitor SB202190 activates MEK/MAPK to stimulate the growth of leukemia cells. Leuk Res. 2009 May; 33(5):693-9, and is represented by the structural formula indicated below:

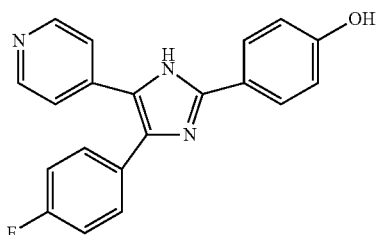

SCIO469 is described in e.g. Sokol L, Cripe L, Kantarjian H, Sekeres M A, Parmar S, Greenberg P, Goldberg S L, Bhushan V, Shammo J, Hohl R, Verma A, Garcia-Manero G, Li Y P, Lowe A, Zhu J, List A F. Randomized, dose-escalation study of the p38-alpha MAPK inhibitor SCIO-469 in patients with myelodysplastic syndrome. Leukemia. 2013 April; 27(4):977-80, and is represented by the structural formula indicated below:

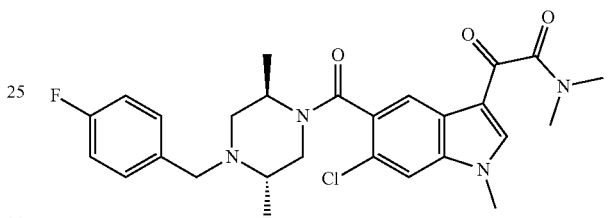

Pharmaceutical Combinations

As outlined above, in a first aspect, the present invention provides a pharmaceutical combination comprising:
(a) a PPAR agonist;
(b) a p38 kinase inhibitor; and optionally
(c) one or more pharmaceutically acceptable diluents, excipients or carriers for use in a method of preventing or treating ophthalmic diseases or disorders in a subject.

Useful PPAR agonists are as defined above. In one embodiment, said PPAR agonist is activating PPAR gamma and/or PPAR alpha. In a preferred embodiment, said PPAR agonist is selected from the group consisting of pioglitazone, rosiglitazone, troglitazone, fenofibrate, bezafibrate and pharmaceutically acceptable salts thereof. In a more preferred embodiment, said PPAR agonist is a PPAR gamma agonist, in particular pioglitazone or a pharmaceutically acceptable salt thereof. In a particularly preferred embodiment, said PPAR agonist is pioglitazone hydrochloride.

Useful p38 kinase inhibitors are as defined above. In a preferred embodiment, said p38 kinase inhibitors are inhibiting p38-alpha, p38-beta, p38-gamma or p38-delta or combinations thereof, preferably inhibiting p38-alpha and/or p38-beta, more preferably inhibiting p38-alpha. Further useful p38 kinase inhibitors are compounds of the formula I or II, or pharmaceutically acceptable salts thereof, as defined supra. Further useful p38 kinase inhibitors are p38 kinase inhibitors selected from the group consisting of pamapimod, acumapimod, losmapimod, dilmapimod, semapimod, AZD7624, ARRY-371797, LY2228820, R9111, PH-797804, BIRB 796, VX-702, VX-745, SB 239063, SB202190, SCIO 469, BMS 582949, and pharmaceutically acceptable salts thereof, in particular pamapimod, losmapimod, LY2228820, BMS 582949 or pharmaceutically acceptable salts and mixtures thereof, more particularly pamapimod or a pharmaceutically acceptable salt thereof.

A pharmaceutical combination according to the invention is for example a combined preparation or a pharmaceutical composition, for simultaneous, separate or sequential use. The term "combined preparation" as used herein defines especially a "kit of parts" in the sense that said PPAR agonist and said p38 inhibitor can be dosed independently, either in separate form e.g. as separate tablets or by use of different fixed combinations with distinguished amounts of the active ingredients. The ratio of the amount of PPAR agonist to the amount of p38 inhibitor to be administered in the combined preparation can be varied, e.g. in order to cope with the needs of a patient sub-population to be treated or the needs of a single patient, which needs can be different due to age, sex, body weight, etc. of a patient. The individual parts of the combined preparation (kit of parts) can be administered simultaneously or sequentially, i.e. chronologically staggered, e.g. at different time points and with equal or different time intervals for any part of the kit of parts.

The term "pharmaceutical composition" refers to a fixed-dose combination (FDC) that includes the PPAR agonist and the p38 inhibitor combined in a single dosage form, having a predetermined combination of respective dosages.

The pharmaceutical combination further may be used as add-on therapy. As used herein, "add-on" or "add-on therapy" means an assemblage of reagents for use in therapy, the subject receiving the therapy begins a first treatment regimen of one or more reagents prior to beginning a second treatment regimen of one or more different reagents in addition to the first treatment regimen, so that not all of the reagents used in the therapy are started at the same time. For example, adding p38 inhibitor therapy to a patient already receiving PPAR agonist therapy and vice versa.

In a particularly preferred embodiment, the pharmaceutical combination according to the invention is a pharmaceutical composition, i.e. a fixed-dose combination.

In a further preferred embodiment, the pharmaceutical combination according to the invention is a combined preparation.

The amount of the PPAR agonist and the p38 inhibitor to be administered will vary depending upon factors such as the particular compound, disease condition and its severity, according to the particular circumstances surrounding the case, including, e.g., the specific PPAR agonist being administered, the route of administration, the condition being treated, the target area being treated, and the subject or host being treated.

In one embodiment, the invention provides a pharmaceutical combination comprising a PPAR agonist and a p38 inhibitor, wherein said PPAR agonist and said p38 inhibitor are present in a therapeutically effective amount.

In a preferred embodiment, the invention provides a pharmaceutical combination comprising a PPAR agonist and a p38 inhibitor, wherein said PPAR agonist and said p38 inhibitor produce a synergistic therapeutic effect i.e. wherein said PPAR agonist and said p38 inhibitor are present in an amount producing a synergistic therapeutic effect.

As used herein, the term "synergistic" means that the effect achieved with the pharmaceutical combinations of this invention is greater than the sum of the effects that result from using the agents, namely the PPAR agonist and the p38 inhibitor, as a monotherapy. Advantageously, such synergy provides greater efficacy at the same doses.

In one embodiment, the invention provides a pharmaceutical combination comprising a p38 inhibitor and a PPAR agonist, wherein the amount of said PPAR agonist in the combination is from about 0.1 to about 20 mg or from about 0.1 to about 15 mg or from about 0.1 to about 10 mg or from about 0.1 to about 7.5 mg or from about 0.1 to about 5 mg or from about 5 to about 15 mg or from about 2 to about 10 mg. In a preferred embodiment, the amount of said PPAR agonist in the combination is from about 2 to about 10 mg, preferably about 5 mg. Where said PPAR agonist is in the form of a pharmaceutically acceptable salt, the amounts of PPAR agonist provided herein are calculated on the basis of the respective free base.

In a preferred embodiment, the invention provides a pharmaceutical combination comprising a p38 inhibitor and a PPAR agonist, wherein the amount of said PPAR agonist in the combination is about 1 mg, about 2 mg, about 3 mg, about 4 mg, about 5 mg, about 6 mg, about 7 mg, about 8 mg, about 9 mg, about 10 mg, about 11 mg or about 12 mg, preferably about 5 mg.

In a particularly preferred embodiment, the invention provides a pharmaceutical combination comprising a p38 inhibitor and pioglitazone or a pharmaceutically acceptable salt thereof, preferably pioglitazone hydrochloride, wherein the amount of pioglitazone in the combination is about 1 mg, about 2 mg, about 3 mg, about 4 mg, about 5 mg, about 6 mg, about 7 mg, about 8 mg, about 9 mg, about 10 mg, about 11 mg or about 12 mg, preferably about 5 mg (based on pioglitazone free base).

In a preferred embodiment, the invention provides a pharmaceutical combination comprising a p38 inhibitor and pioglitazone or a pharmaceutically acceptable salt thereof, wherein the amount of pioglitazone or a pharmaceutically acceptable salt thereof in the combination is below the dose typically needed for the treatment of diabetes with pioglitazone or a pharmaceutically acceptable salt thereof.

In one embodiment, the invention provides a pharmaceutical combination comprising a p38 inhibitor and a PPAR agonist, wherein the amount of said p38 inhibitor in the combination is from about 1 to about 500 mg or from about 1 to about 450 mg or from about 1 to about 400 mg or from about 1 to about 350 mg or from about 1 to about 300 mg or from about 1 to about 250 mg or from about 1 to about 200 mg or from about 1 to about 150 mg or from about 1 to about 125 mg or from about 1 to about 100 mg or from about 10 to about 125 mg or from about 10 to about 100 mg or from about 20 to about 100 mg or from about 30 to about 100 mg or from about 40 to about 100 mg or from about 50 to about 100 mg, or from about 75 to about 100 mg.

In a preferred embodiment, the invention provides a pharmaceutical combination comprising a p38 inhibitor and a PPAR agonist, wherein the amount of said p38 inhibitor in the combination is about 25 mg, about 50 mg, about 75 mg, about 125 mg, about 150 mg or about 300 mg.

In a further preferred embodiment, the invention provides a pharmaceutical combination comprising a p38 inhibitor and a PPAR agonist, wherein the amount of said p38 inhibitor in the combination is about 2 mg, about 6 mg, about 12 mg, about 25 mg, about 50 mg, about 75 mg or about 150 mg.

In a particularly preferred embodiment, the invention provides a pharmaceutical combination comprising a p38 inhibitor and a PPAR agonist, wherein the amount of said p38 inhibitor in the combination is about 50 mg, about 75 mg or about 150 mg, most preferably about 75 mg.

In a particularly preferred embodiment, the invention provides a pharmaceutical combination comprising pamapimod or a pharmaceutically acceptable salt thereof and a PPAR agonist, wherein the amount of pamapimod in the combination is about 2 mg, about 6 mg, about 12 mg, about 25 mg, about 50 mg, about 75 mg or about 150 mg.

In one embodiment, the invention provides a pharmaceutical combination comprising a p38 inhibitor and a PPAR agonist, wherein the amount of said PPAR agonist in the combination is from about 0.1 to about 20 mg or from about 0.1 to about 15 mg or from about 0.1 to about 10 mg or from about 0.1 to about 7.5 mg or from about 0.1 to about 5 mg or from about 1 to about 15 mg or from about 2 to about 10 mg; and wherein the amount of said p38 inhibitor in the combination is from about 1 to about 500 mg or from about 1 to about 450 mg or from about 1 to about 400 mg or from about 1 to about 350 mg or from about 1 to about 300 mg or from about 1 to about 250 mg or from about 1 to about 200 mg or from about 1 to about 150 mg or from about 1 to about 125 mg or from about 1 to about 100 mg or from about 10 to about 125 mg or from about 10 to about 100 mg or from about 20 to about 100 mg or from about 30 to about 100 mg or from about 40 to about 100 mg or from about 50 to about 100 mg, or from about 75 to about 100 mg.

In a preferred embodiment, the invention provides a pharmaceutical combination comprising a p38 inhibitor and a PPAR agonist, wherein the amount of said PPAR agonist in the combination is about 1 mg, about 2 mg, about 3 mg, about 4 mg, about 5 mg, about 6 mg, about 7 mg, about 8 mg, about 9 mg, about 10 mg, about 11 mg or about 12 mg; and wherein the amount of said p38 inhibitor in the combination is about 2 mg, about 6 mg, about 12 mg, about 25 mg, about 50 mg, about 75 mg or about 150 mg.

In a particularly preferred embodiment, the invention provides a pharmaceutical combination comprising pamapimod or a pharmaceutically acceptable salt thereof and pioglitazone or a pharmaceutically acceptable salt thereof (e.g. pioglitazone hydrochloride), wherein the amount of pamapimod or a pharmaceutically acceptable salt thereof in the combination is from about 30 to about 100 mg, preferably from about 40 to about 80 mg, most preferably about 75 mg (based on pamapimod free base); and wherein the amount of pioglitazone or a pharmaceutically acceptable salt thereof in the combination is from about 0.5 to about 10 mg, preferably from about 0.5 to about 7.5 mg, most preferably about 5 mg; (based on pioglitazone free base).

In a preferred embodiment, the pharmaceutical combination of the invention is a pharmaceutical composition (i.e. a fixed-dose combination, as outlined above). In one embodiment, the pharmaceutical combination of the invention is a pharmaceutical composition and includes other medicinal or pharmaceutical agents, e.g., one or more pharmaceutically acceptable diluents, excipients or carriers.

Compounds of Formula I for Use in a Method of Preventing or Treating Ophthalmic Diseases or Disorders in a Subject As indicated above, compounds of formula I or pharmaceutically acceptable salts thereof alone i.e., not in combination with a PPAR agonist, are useful for preventing or treating ophthalmic diseases or disorders.

Accordingly, in one aspect, the present invention provides a compound of formula I

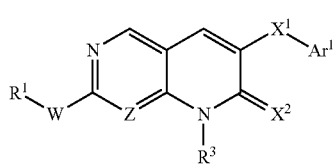

Formula I or a pharmaceutically acceptable salt thereof, wherein
Z is N or CH;
W is $NR^2$;
X' is O, $NR^4$ (where $R^4$ is hydrogen or alkyl), S, or $CR^5R^6$ (where $R^5$ and $R^6$ are independently hydrogen or alkyl) or C=O;
$X^2$ is O or $NR^7$;
$Ar^1$ is aryl or heteroaryl;
$R^2$ is hydrogen, alkyl, acyl, alkoxycarbonyl, aryloxycarbonyl, heteroalkylcarbonyl, heteroalkyloxycarbonyl or —$R^{21}$—$R^{22}$ where $R^{21}$ is alkylene or —C(=O)— and $R^{22}$ is alkyl or alkoxy;
$R^1$ is hydrogen, alkyl, haloalkyl, aryl, aralkyl, heteroaryl, heteroaralkyl, cycloalkyl, cycloalkylalkyl, heteroalkyl-substituted cycloalkyl, heterosubstituted cycloalkyl, heteroalkyl, cyanoalkyl, heterocyclyl, heterocyclylalkyl, $R^{12}$—$SO_2$-heterocycloamino (where $R^{12}$ is haloalkyl, aryl, aralkyl, heteroaryl or heteroaralkyl), —$Y^1$—C(O)—$Y^2$—$R^{11}$ (where $Y^1$ and $Y^2$ are independently either absent or an alkylene group and $R^{11}$ is hydrogen, alkyl, haloalkyl, hydroxy, alkoxy, amino, monoalkylamino or dialkylamino), (heterocyclyl)(cycloalkyl)alkyl or (heterocyclyl)(heteroaryl)alkyl;
$R^3$ is hydrogen, alkyl, cycloalkyl, cycloalkylalkyl, aryl, aralkyl, haloalkyl, heteroalkyl, cyanoalkyl, alkylene-C(O)—$R^{31}$ (where $R^{31}$ is hydrogen, alkyl, hydroxy, alkoxy, amino, monoalkylamino or dialkylamino), amino, monoalkylamino, dialkylamino or $NR^{32}$—$Y^3$—$R^{33}$ (where $Y^3$ is —C(O), —C(O)O—, —C(O)$NR^{34}$, $S(O)_2$ or $S(O)_2NR^{35}$; $R^{32}$, $R^{34}$ and $R^{35}$ are independently hydrogen or alkyl; and $R^{33}$ is hydrogen, alkyl, cycloalkyl, cycloalkylalkyl, heteroalkyl or optionally substituted phenyl) or acyl; and
$R^7$ is hydrogen or alkyl;

and optionally one or more pharmaceutically acceptable diluents, excipients or carriers for use in a method of preventing or treating ophthalmic diseases or disorders in a subject.

In one embodiment, the present invention provides a compound of formula I or a pharmaceutically acceptable salt thereof for use in a method of preventing or treating ophthalmic diseases or disorders in a subject, wherein $X^1$ is $NR^4$ and $X^2$ is $NR^7$ or $X^1$ and $X^2$ are each O, wherein $R^4$ and $R^7$ are as defined above.

In a further embodiment, the present invention provides a compound of formula I or a pharmaceutically acceptable salt thereof for use in a method of preventing or treating ophthalmic diseases or disorders in a subject, wherein $X^1$ is $NR^4$ or O and $X^2$ is $NR^7$ or O, wherein $R^4$ and $R^7$ are as defined above.

In a further embodiment, the present invention provides a compound of formula I or a pharmaceutically acceptable salt thereof for use in a method of preventing or treating ophthalmic diseases or disorders in a subject, wherein W is $NR^2$, and wherein $R^2$ is hydrogen, alkyl, heteroalkyl, acyl or alkoxycarbonyl, preferably hydrogen or alkyl, more preferably hydrogen.

In yet a further embodiment, the present invention provides a compound of formula I or a pharmaceutically acceptable salt thereof for use in a method of preventing or treating ophthalmic diseases or disorders in a subject, wherein $R^1$ is hydrogen, alkyl, haloalkyl, cycloalkyl, cycloalkylalkyl, heteroalkylsubstituted cycloalkyl, heterosubstituted cycloalkyl, heteroalkyl, cyanoalkyl, heterocyclyl, heterocyclylalkyl or (heterocyclyl)(cycloalkyl)alkyl.

In a preferred embodiment, the present invention provides a compound of formula I or a pharmaceutically acceptable salt thereof for use in a method of preventing or treating ophthalmic diseases or disorders in a subject, wherein $R^2$ is hydrogen and $R^1$ is heteroalkyl or vice versa.

In yet a further embodiment, the present invention provides a compound of formula I or a pharmaceutically acceptable salt thereof for use in a method of preventing or treating ophthalmic diseases or disorders in a subject, wherein $R^1$ is hydrogen, alkyl, haloalkyl, heteroalkyl or cyanoalkyl.

In yet a further embodiment, the present invention provides a compound of formula I or a pharmaceutically acceptable salt thereof for use in a method of preventing or treating ophthalmic diseases or disorders in a subject, wherein $R^1$ is cycloalkyl, cycloalkylalkyl, heteroalkylsubstituted cycloalkyl, heterosubstituted cycloalkyl, heterocyclyl, heterocyclylalkyl or (heterocyclyl)(cycloalkyl)alkyl.

In a preferred embodiment, the present invention provides a compound of formula I or a pharmaceutically acceptable salt thereof for use in a method of preventing or treating ophthalmic diseases or disorders in a subject, wherein each of $R^1$ and $R^2$ is independently selected from hydrogen and hydroxyalkyl, preferably from hydrogen, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 3,3-dihydroxybutyl, 3,4-dihydroxybutyl, 2-(hydroxymethyl)-3-hydroxypropyl, 3-hydroxy-1-(2-hydroxyethyl)-propyl and 2-hydroxy-1-methylethyl, more preferably from hydrogen, 2-hydroxyethyl, 2,3-dihydroxypropyl and 1-(hydroxymethyl)2-hydroxyethyl, most preferably from hydrogen, 2-hydroxypropyl, 3-hydroxy-1-(2-hydroxyethyl)-propyl and 2-hydroxy-1-methylethyl.

In yet a further embodiment, the present invention provides a compound of formula I or a pharmaceutically acceptable salt thereof for use in a method of preventing or treating ophthalmic diseases or disorders in a subject, wherein $R^3$ is hydrogen, alkyl, cycloalkyl, cycloalkylalkyl, haloalkyl, heteroalkyl, cyanoalkyl, alkylene-C(O)—$R^{31}$ (where $R^{31}$ is hydrogen, alkyl, hydroxy, alkoxy, amino, monoalkylamino or dialkylamino) or acyl.

In yet a further embodiment, the present invention provides a compound of formula I or a pharmaceutically acceptable salt thereof for use in a method of preventing or treating ophthalmic diseases or disorders in a subject, wherein $R^3$ is hydrogen, alkyl, haloalkyl, heteroalkyl, cyanoalkyl, cycloalkyl or cycloalkylalkyl.

In yet a further embodiment, the present invention provides a compound of formula I or a pharmaceutically acceptable salt thereof for use in a method of preventing or treating ophthalmic diseases or disorders in a subject, wherein $R^3$ is alkyl, haloalkyl, heteroalkyl or cyanoalkyl.

In yet a further embodiment, the present invention provides a compound of formula I or a pharmaceutically acceptable salt thereof for use in a method of preventing or treating ophthalmic diseases or disorders in a subject, wherein $R^3$ is cycloalkyl or cycloalkylalkyl.

In yet a further embodiment, the present invention provides a compound of formula I or a pharmaceutically acceptable salt thereof for use in a method of preventing or treating ophthalmic diseases or disorders in a subject, wherein $X^1$ and $X^2$ are both O.

In yet a further embodiment, the present invention provides a compound of formula I or a pharmaceutically acceptable salt thereof for use in a method of preventing or treating ophthalmic diseases or disorders in a subject, wherein $R^1$ is alkyl or heteroalkyl.

In yet a further embodiment, the present invention provides a compound of formula I or a pharmaceutically acceptable salt thereof for use in a method of preventing or treating ophthalmic diseases or disorders in a subject, wherein $R^1$ is heteroalkyl, preferably 3-hydroxy-1-(2-hydroxyethyl)-propyl or 2-hydroxy-1-methylethyl.

In yet a further embodiment, the present invention provides a compound of formula I or a pharmaceutically acceptable salt thereof for use in a method of preventing or treating ophthalmic diseases or disorders in a subject, wherein $R^3$ is alkyl or heteroalkyl.

In yet a further embodiment, the present invention provides a compound of formula I or a pharmaceutically acceptable salt thereof for use in a method of preventing or treating ophthalmic diseases or disorders in a subject, wherein $R^3$ is alkyl, preferably C1-C5 alkyl, more preferably C1-C4 alkyl, more preferably C1-C3 alkyl. In a particularly preferred embodiment, $R^3$ is ethyl or methyl, preferably methyl.

In yet a further embodiment, the present invention provides a compound of formula I or a pharmaceutically acceptable salt thereof for use in a method of preventing or treating ophthalmic diseases or disorders in a subject, wherein $R^3$ is heteroalkyl, preferably 2-hydroxy-propyl.

In yet a further embodiment, the present invention provides a compound of formula I or a pharmaceutically acceptable salt thereof for use in a method of preventing or treating ophthalmic diseases or disorders in a subject, wherein W is NH.

In yet a further embodiment, the present invention provides a compound of formula I or a pharmaceutically acceptable salt thereof for use in a method of preventing or treating ophthalmic diseases or disorders in a subject, wherein Z is N.

In yet a further embodiment, the present invention provides a compound of formula I or a pharmaceutically acceptable salt thereof for use in a method of preventing or treating ophthalmic diseases or disorders in a subject, wherein $Ar^1$ is aryl, preferably phenyl optionally substituted with one, two or three halo substituents, most preferably phenyl substituted with two halo substituents in ortho and para position. In a particularly preferred embodiment, $Ar^1$ is 2,4-difluorophenyl.

In yet a further embodiment, the present invention provides a compound of formula I or a pharmaceutically acceptable salt thereof for use in a method of preventing or treating ophthalmic diseases or disorders in a subject, wherein $X^1$ is $NR^4$ and $X^2$ is $NR^7$ or $X^1$ and $X^2$ are each O, wherein $R^4$ and $R^7$ are as defined above; and wherein
  $R^1$ is hydrogen, alkyl, haloalkyl, cycloalkyl, cycloalkylalkyl, heteroalkylsubstituted cycloalkyl, heterosubstituted cycloalkyl, heteroalkyl, cyanoalkyl, heterocyclyl, heterocyclylalkyl or (heterocyclyl)(cycloalkyl)alkyl; and wherein
  $R^3$ is hydrogen, alkyl, cycloalkyl, cycloalkylalkyl, haloalkyl, heteroalkyl, cyanoalkyl, alkylene-C(O)—$R^{31}$ (where $R^{31}$ is hydrogen, alkyl, hydroxy, alkoxy, amino, monoalkylamino or dialkylamino) or acyl; and wherein
  W is $NR^2$, wherein $R^2$ is hydrogen, alkyl, acyl or alkoxycarbonyl; and wherein
  $Ar^1$ is aryl; and wherein
  Z is N.

In a preferred embodiment, the present invention provides a compound of formula I or a pharmaceutically acceptable salt thereof for use in a method of preventing or treating ophthalmic diseases or disorders in a subject, wherein $X^1$ and $X^2$ are each O and wherein Z is N and wherein W is NH and wherein Ar¹ is phenyl optionally substituted by one, two or three halo substituents and wherein R¹ is heteroalkyl and wherein R³ is alkyl or heteroalkyl.

In a particularly preferred embodiment, the present invention provides a compound of formula I or a pharmaceutically acceptable salt thereof for use in a method of preventing or treating ophthalmic diseases or disorders in a subject, wherein said compound of formula I is pamapimod (6-(2,4-Difluorophenoxy)-2-[3-hydroxy-1-(2-hydroxyethyl)-propylamino]-8-methyl-8H-pyrido[2,3-d]pyrimidin-7-one, Formula III).

Formula III

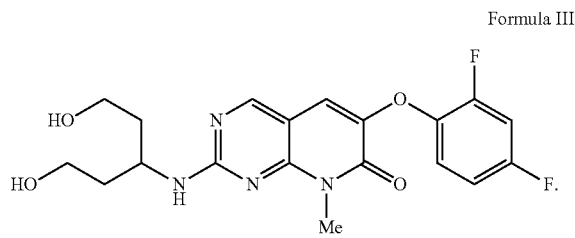 [SMILES: Cn1c(=O)c(Oc2ccc(F)cc2F)cc2cnc(NC(CCO)CCO)nc21]

In one aspect, the present invention provides a pharmaceutical composition comprising
(a) a compound of formula I or a pharmaceutically acceptable salt thereof as defined supra; and optionally
(b) one or more pharmaceutically acceptable diluents, excipients or carriers for use in a method of preventing or treating ophthalmic diseases or disorders in a subject.

In one embodiment, the invention provides a pharmaceutical composition comprising a compound of formula I or a pharmaceutically acceptable salt thereof, wherein the amount of said compound of formula I or a pharmaceutically acceptable salt thereof in the composition is from about 1 to about 500 mg or from about 1 to about 450 mg or from about 1 to about 400 mg or from about 1 to about 350 mg or from about 1 to about 300 mg or from about 1 to about 250 mg or from about 1 to about 200 mg or from about 1 to about 150 mg or from about 1 to about 125 mg or from about 1 to about 100 mg or from about 10 to about 125 mg or from about 10 to about 100 mg or from about 20 to about 100 mg or from about 30 to about 100 mg or from about 40 to about 100 mg or from about 50 to about 100 mg, or from about 75 to about 100 mg.

In a preferred embodiment, the invention provides a pharmaceutical composition comprising a compound of formula I or a pharmaceutically acceptable salt thereof, wherein the amount of said compound of formula I or a pharmaceutically acceptable salt thereof in the composition is about 25 mg, about 50 mg, about 75 mg, about 125 mg, about 150 mg or about 300 mg.

In a further preferred embodiment, the invention provides a pharmaceutical composition comprising a compound of formula I or a pharmaceutically acceptable salt thereof, wherein the amount of said compound of formula I or a pharmaceutically acceptable salt thereof in the composition is about 2 mg, about 6 mg, about 12 mg, about 25 mg, about 50 mg, about 75 mg or about 150 mg.

In a particularly preferred embodiment, the invention provides a pharmaceutical composition comprising a compound of formula I or a pharmaceutically acceptable salt thereof, wherein the amount of said compound of formula I or a pharmaceutically acceptable salt thereof in the composition is about 50 mg, about 75 mg or about 150 mg, most preferably about 75 mg.

Modes of Administration and Treatment

The terms "treatment"/"treating" as used herein includes: (1) delaying the appearance of clinical symptoms of the state, disorder or condition developing in an animal, particularly a mammal and especially a human, that may be afflicted with or predisposed to the state, disorder or condition but does not yet experience or display clinical or subclinical symptoms of the state, disorder or condition; (2) inhibiting the state, disorder or condition (e.g. arresting, reducing or delaying the progression of the disease, or a relapse thereof in case of maintenance treatment, of at least one clinical or subclinical symptom thereof); and/or (3) relieving the condition (i.e. causing regression of the state, disorder or condition or at least one of its clinical or subclinical symptoms). The benefit to a patient to be treated is either statistically significant or at least perceptible to the patient or to the physician. However, it will be appreciated that when a medicament is administered to a patient to treat a disease, the outcome may not always be effective treatment.

As used herein, "delay of progression" means increasing the time to appearance of a symptom of ophthalmic diseases or disorders or a mark associated with ophthalmic diseases or disorders or slowing the increase in severity of a symptom of ophthalmic diseases or disorders. Further, "delay of progression" as used herein includes reversing or inhibition of disease progression. "Inhibition" of disease progression or disease complication in a subject means preventing or reducing the disease progression and/or disease complication in the subject.

Preventive treatments comprise prophylactic treatments. In preventive applications, the pharmaceutical combination of the invention or a compound of formula I or a pharmaceutically acceptable salt thereof is administered to a subject suspected of having, or being at risk for developing ophthalmic diseases or disorders. In therapeutic applications, the pharmaceutical combination of the invention or a compound of formula I or a pharmaceutically acceptable salt thereof is administered to a subject such as a patient already suffering from ophthalmic diseases or disorders, in an amount sufficient to cure or at least partially arrest the symptoms of the disease. Amounts effective for this use will depend on the severity and course of the disease, previous therapy, the subject's health status and response to the drugs, and the judgment of the treating physician. In the case wherein the subject's condition does not improve, the pharmaceutical combination of the invention or a compound of formula I or a pharmaceutically acceptable salt thereof may be administered chronically, which is, for an extended period of time, including throughout the duration of the subject's life in order to ameliorate or otherwise control or limit the symptoms of the subject's disease or condition.

In the case wherein the subject's status does improve, the pharmaceutical combination of the invention or a compound of formula I or a pharmaceutically acceptable salt thereof may be administered continuously; alternatively, the dose of drugs being administered may be temporarily reduced or temporarily suspended for a certain length of time (i.e., a "drug holiday").

The pharmaceutical combination or a compound of formula I or a pharmaceutically acceptable salt thereof according to the invention is, preferably, suitable for oral, topical, injectable, ocular, local ocular (e.g., subconjunctival, intravitreal, retrobulbar or intracameral) or systemic (i.e. enteral or parenteral) administration more preferably suitable for oral, topical, and/or injectable, most preferably suitable for oral administration to a subject and comprises a therapeutically effective amount of the active ingredient(s) and one or more suitable pharmaceutically acceptable diluents, excipients or carriers.

If not indicated otherwise, a pharmaceutical combination or a compound of formula I or a pharmaceutically acceptable salt thereof according to the invention is prepared in a manner known per se, e.g. by means of conventional mixing, granulating, coating, dissolving or lyophilizing processes. In preparing a combination for an oral dosage form, any of the usual pharmaceutical media may be employed, carriers, diluents, granulating agents, lubricants, binders, disintegrating agents and the like. Because of their ease of administration, tablets and capsules represent the most advantageous oral dosage unit forms, in which case solid pharmaceutical carriers are obviously employed.

In one embodiment, the pharmaceutical combination or a compound of formula I or a pharmaceutically acceptable salt thereof according to the invention is a combination for oral administration. As indicated above, said pharmaceutical combination for oral administration is preferably a pharmaceutical composition, i.e. a fixed-dose combination.

In one embodiment, the pharmaceutical combination or a compound of formula I or a pharmaceutically acceptable salt thereof according to the invention is a combination for topical ocular administration. As indicated above, said pharmaceutical combination for topical ocular administration is preferably a pharmaceutical composition, i.e. a fixed-dose combination.

In one embodiment, the pharmaceutical combination or a compound of formula I or a pharmaceutically acceptable salt thereof according to the invention is a combination for injectable administration. As indicated above, said pharmaceutical combination for injectable administration is preferably a pharmaceutical composition, i.e. a fixed-dose combination.

In one embodiment, the pharmaceutical combination or a compound of formula I or a pharmaceutically acceptable salt thereof according to the invention is a combination for local ocular administration. As indicated above, said pharmaceutical combination for local ocular administration is preferably a pharmaceutical composition, i.e. a fixed-dose combination.

In one embodiment, the pharmaceutical combination or a compound of formula I or a pharmaceutically acceptable salt thereof according to the invention is a combination for systemic, i.e. enteral or parenteral administration. Preferred are combinations for oral administration. As indicated above, said pharmaceutical combination for systemic administration is preferably a pharmaceutical composition, i.e. a fixed-dose combination.

In a preferred embodiment the pharmaceutical combination or a compound of formula I or a pharmaceutically acceptable salt thereof according to the invention is administered orally, topically or by injection, more preferably orally to the subject.

A pharmaceutical combination or a compound of formula I or a pharmaceutically acceptable salt thereof for oral or systemic i.e. enteral or parenteral administration is, for example, a unit dosage form, such as a tablet, a capsule or a suppository.

In one embodiment, the invention provides a pharmaceutical composition comprising a PPAR agonist, such as pioglitazone and a p38 inhibitor, such as pamapimod and at least one pharmaceutically acceptable carrier, wherein the composition is a solution or a suspension for ocular administration (i.e. eye drops), or an ophthalmic ointment.

In one embodiment, the invention provides a pharmaceutical composition comprising pamapimod or a pharmaceutically acceptable salt thereof and at least one pharmaceutically acceptable carrier, wherein the composition is a solution or a suspension for ocular administration (i.e. eye drops), or an ophthalmic ointment.

In one embodiment, the invention provides a pharmaceutical composition comprising a PPAR agonist, such as pioglitazone and a p38 inhibitor, such as pamapimod and at least one pharmaceutically acceptable carrier, wherein the composition is a tablet or a capsule, preferably a tablet.

In one embodiment, the invention provides a pharmaceutical composition comprising pamapimod or a pharmaceutically acceptable salt thereof and at least one pharmaceutically acceptable carrier, wherein the composition is a tablet or a capsule, preferably a tablet.

In a further embodiment, the pharmaceutical combination of the invention is suitable for ocular administration to deliver said PPAR agonist and said p38 kinase inhibitor to the eye(s) of the subject. Similarly, in a further embodiment, the inventive pharmaceutical composition comprising a compound of formula I or a pharmaceutically acceptable salt thereof is suitable for ocular administration to deliver said compound of formula I or said pharmaceutically acceptable salt thereof to the eye(s) of the subject.

The unit content of active ingredients in an individual dose need not in itself constitute a therapeutically effective amount, since such an amount can be reached by the administration of a plurality of dosage units. A composition according to the invention may contain, e.g., from about 10% to about 100% of the therapeutically effective amount of the active ingredients.

Where the pharmaceutical combination according to the invention is a combined preparation, said PPAR agonist need not be administered in the same dosage form as said p38 inhibitor.

In some embodiments the pharmaceutical combination of the invention is administered to the subject in a dose that comprises a dose of a PPAR agonist which is below the dose needed for the treatment of diabetes using said PPAR agonist. In some embodiments the pharmaceutical combination of the invention is administered to the subject in a dose that comprises a dose of a PPAR agonist which is a factor of 8-20 fold lower than the top dose evaluated and tested for the treatment of diabetes, in particular a factor of 8-20 fold lower than the top dose evaluated and tested for the treatment of diabetes in human. The top dose evaluated and tested for the treatment of diabetes in human, e.g for a PPAR gamma agonists such as pioglitazone hydrochloride, is usually in the range of about 30-45 mg/day. In some embodiments at the PPAR agonist dose used, the side effects seen in the treatment of diabetes using said PPAR agonist are reduced or not present.

In some embodiments the pharmaceutical combination of the invention is administered to the subject in a dose that comprises a dose of a PPAR agonist which is below the active dose for therapeutically relevant antidiabetic or anti-dyslipidemic effect of the PPAR agonist, in particular a dose that is below the active dose for antidiabetic or anti-dyslipidemic effect of the PPAR agonist in human.

A typical dosing regimen of pioglitazone or a pharmaceutically acceptable salt thereof in the treatment of diabetes includes 15 to 45 mg pioglitazone once-daily.

In some embodiments, the pharmaceutical combination of the invention is administered orally to a human in a dose comprising a dose of a PPAR agonist, usually PPAR gamma agonists, PPAR alpha agonists and/or PPAR alpha/gamma dual agonists, preferably a PPAR gamma agonist and/or a PPAR alpha agonist, more preferably a PPAR gamma agonist and/or a PPAR alpha agonist selected from the group consisting of pioglitazone, rosiglitazone, troglitazone, feonofibrate, bezafibrate and pharmaceutically acceptable salts thereof, even more preferably a PPAR gamma agonist, yet more preferably pioglitazone or a pharmaceutically acceptable salt thereof, most preferably pioglitazone hydrochloride of 0.1-45 mg/day, preferably 0.1-10 mg/day, more preferably about 5 mg/day; and comprising a dose of a p38 inhibitor, e.g. a compound of formula I or II, in particular a compound of formula I, preferably a p38 inhibitor selected from the group consisting of pamapimod, acumapimod, losmapimod, dilmapimod, semapimod, AZD7624, ARRY-371797, LY2228820, R9111, PH-797804, BIRB 796, VX-702, VX-745 SB 239063, SB202190, SCIO 469, and BMS 582949 or a pharmaceutically acceptable salt thereof, more preferably pamapimod or a pharmaceutically acceptable salt thereof of 1-500 mg/day, preferably 10-250 mg/day, more preferably 25-150 mg/day, most preferably about 75 mg/day.

Methods of identification of patients who are suspected of having, or being at risk for developing an ophthalmic disease or disorder are also comprised by the present invention. In some embodiments patients who are suspected of having, or being at risk for developing an ophthalmic disease or disorder are identified by e.g. blood tests, eye test e.g. visual activity or fundus imaging. In some embodiments the monitoring of the treatment success and/or the identification of the subject, e.g. the identification of the subject who is suspected of having, or being at risk for developing ophthalmic disease or disorder, is achieved by improvement in visual symptoms such as less distorted vision (metamorphopsia), faster recovery of visual function after exposure to bright light (photostress test), increase in visual acuity, less blurred vision, better ability to discern colors (specifically dark ones from dark ones and light ones from light ones), improvement in contrast sensitivity and the like.

Dosing Regimen

An exemplary treatment regime entails administration once daily, twice daily, or thrice daily every second day, preferably once daily and/or twice daily. The combination of the invention is usually administered on multiple occasions. Intervals between single dosages can be, for example, less than a day, daily, or every second day. The combination of the invention may be given as a continous uninterrupted treatment. The combination of the invention may also be given in a regime in which the subject receives cycles of treatment interrupted by a drug holiday or period of non-treatment. Thus, the combination of the invention may be administered according to the selected intervals above for a continuous period of one week or a part thereof, for two weeks, for three weeks, for four weeks, for five weeks or for six weeks and then stopped for a period of one week, or a part thereof, for two weeks, for three weeks, for four weeks, for five weeks, or for six weeks. The combination of the treatment interval and the non-treatment interval is called a cycle. The cycle may be repeated one or more times. Two or more different cycles may be used in combination for repeating the treatment one or more times. Intervals can also be irregular and guided either by worseining or improvement in the condition of the patient indicated by appearance or remission of symptoms or objective evidence of disease appearance or remission. In such case, therapy may be started and suspended as needed, and only restarted when symptoms or objective measures indicate the return of disease. In a preferred embodiment, the pharmaceutical combination according to the invention is administered once daily.

Kits/Articles of Manufacture

In one aspect, the present invention also provides a kit for use in a method of preventing or treating ophthalmic diseases or disorders in a subject, comprising a pharmaceutical combination disclosed herein, and instructions for using the kit. Preferred PPAR agonists and preferred p38 kinase inhibitors comprised by said pharmaceutical combination are as described above.

In some embodiments, kits include a carrier, package, or container that is compartmentalized to receive one or more containers such as vials, tubes, and the like, each of the container(s) including one of the separate elements to be used in a method described herein. Suitable containers include, for example, bottles, vials, syringes, and test tubes. In other embodiments, the containers are formed from a variety of materials such as glass or plastic.

The articles of manufacture provided herein generally will comprise one or more pharmaceutical combination disclosed herein and packaging materials. Examples of pharmaceutical packaging materials include, but are not limited to, blister packs, bottles, tubes, inhalers, pumps, bags, vials, containers, syringes, and any packaging material suitable for a selected composition and intended mode of administration and treatment.

Preventing or Treating Ophthalmic Diseases or Disorders

In one aspect, the present invention provides a pharmaceutical combination described herein, i.e. a pharmaceutical combination comprising:
(a) a PPAR agonist;
(b) a p38 kinase inhibitor; and optionally
(c) one or more pharmaceutically acceptable diluents, excipients or carriers for use in a method of preventing or treating ophthalmic diseases or disorders in a subject.

Also provided is the use of a pharmaceutical combination described herein for the manufacture of a medicament for preventing or treating ophthalmic diseases or disorders in a subject.

Also provided is the use of a pharmaceutical combination described herein for preventing or treating ophthalmic diseases or disorders in a subject.

Also provided is a method of preventing or treating ophthalmic diseases or disorders in a subject, comprising administering to said subject a therapeutically effective amount of a pharmaceutical combination as described herein.

As indicated above, it has unexpectedly been found that compounds of formula I or pharmaceutically acceptable salts thereof alone, i.e. not in combination with a PPAR agonist, are useful for preventing or treating ophthalmic diseases or disorders. Thus, in a further aspect, the present invention provides a compound of formula I, or a pharmaceutically acceptable salt thereof for use in a method of preventing or treating ophthalmic diseases or disorders in a subject.

Also provided is the use of a compound of formula I, or a pharmaceutically acceptable salt thereof for the manufacture of a medicament for preventing or treating ophthalmic diseases or disorders in a subject.

Also provided is the use of a compound of formula I, or a pharmaceutically acceptable salt thereof for preventing or treating ophthalmic diseases or disorders in a subject.

Also provided is a method of preventing or treating ophthalmic diseases or disorders in a subject, comprising administering to said subject a therapeutically effective amount of a compound of formula I, or a pharmaceutically acceptable salt thereof.

In one embodiment, the present invention provides a pharmaceutical combination described herein or a compound of formula I, or a pharmaceutically acceptable salt thereof for use in a method of preventing or treating ophthalmic diseases or disorders in a subject, wherein said ophthalmic disease or disorder is macular degeneration, preferably macular degeneration selected from age-related macular degeneration (AMD), hereditary macular degeneration (juvenile macular degeneration), such as retinitis pigmentosa (retinopathia pigmentosa), morbus Best, morbus Stargardt and Sorsby's disease, diabetic retinopathy (retinopathia diabetica), myopic macular degeneration, macular degeneration due to inflammation (retinitis), such as presumed ocular histoplasmosis syndrome (POHS) and retinal toxicosis of systemic medications, e.g. chloroquine retinopathy (bull's eye maculopathy).

In a further embodiment, the present invention provides a pharmaceutical combination described herein or a compound of formula I, or a pharmaceutically acceptable salt thereof for use in a method of preventing or treating ophthalmic diseases or disorders in a subject, wherein said ophthalmic disease or disorder is selected from age-related macular degeneration (AMD), hereditary macular degeneration (juvenile macular degeneration) e.g. retinitis pigmentosa (retinopathia pigmentosa), morbus Best, morbus Stargardt and Sorsby's disease, diabetic retinopathy (retinopathia diabetica), myopic macular degeneration, macular degeneration due to inflammation (retinitis) e.g. presumed ocular histoplasmosis syndrome (POHS), and retinal toxicosis of systemic medications, e.g. chloroquine retinopathy (bull's eye maculopathy).

In a further embodiment, the present invention provides a pharmaceutical combination described herein or a compound of formula I, or a pharmaceutically acceptable salt thereof for use in a method of preventing or treating ophthalmic diseases or disorders in a subject, wherein said ophthalmic disease or disorder is selected from the group consisting of, uveoretinitis, retinitis, immunological, chorioditis, age-related macular degeneration, and glaucoma.

In a further embodiment, the present invention provides a pharmaceutical combination described herein or a compound of formula I, or a pharmaceutically acceptable salt thereof for use in a method of preventing or treating ophthalmic diseases or disorders in a subject, wherein said ophthalmic disease or disorder is selected from the group consisting of age-related macular degeneration, exudative macular degeneration, atrophic macular degeneration, retinal toxicosis of systemic medications, and macular edema.

In a further embodiment, the present invention provides a pharmaceutical combination described herein or a compound of formula I, or a pharmaceutically acceptable salt thereof for use in a method of preventing or treating ophthalmic diseases or disorders in a subject, wherein said ophthalmic disease or disorder is selected from wet (exudative) age-related macular degeneration, dry (non-exudative) age-related macular degeneration, geographic atrophy (GA), retinitis pigmentosa (retinopathia pigmentosa), morbus Stargardt and diabetic retinopathy (retinopathia diabetica).

In a preferred embodiment, the present invention provides a pharmaceutical combination described herein or a compound of formula I, or a pharmaceutically acceptable salt thereof for use in a method of preventing or treating ophthalmic diseases or disorders in a subject, wherein said ophthalmic disease or disorder is age-related macular degeneration (AMD).

In a further preferred embodiment, the present invention provides a pharmaceutical combination described herein or a compound of formula I, or a pharmaceutically acceptable salt thereof for use in a method of preventing or treating ophthalmic diseases or disorders is wet (exudative) age-related macular degeneration, dry (non-exudative) age-related macular degeneration or geographic atrophy.

In a particularly preferred embodiment, the present invention provides a pharmaceutical combination described herein or a compound of formula I, or a pharmaceutically acceptable salt thereof for use in a method of preventing or treating ophthalmic diseases or disorders in a subject, wherein said ophthalmic disease or disorder is wet (exudative) age-related macular degeneration.

In a further particularly preferred embodiment, the present invention provides a pharmaceutical combination described herein or a compound of formula I, or a pharmaceutically acceptable salt thereof for use in a method of preventing or treating ophthalmic diseases or disorders in a subject, wherein said ophthalmic disease or disorder is dry (non-exudative) age-related macular degeneration.

In a further particularly preferred embodiment, the present invention provides a pharmaceutical combination described herein or a compound of formula I, or a pharmaceutically acceptable salt thereof for use in a method of preventing or treating ophthalmic diseases or disorders in a subject, wherein said ophthalmic disease or disorder is geographic atrophy.

In a further particularly preferred embodiment, the present invention provides a pharmaceutical combination described herein or a compound of formula I, or a pharmaceutically acceptable salt thereof for use in a method of preventing or treating ophthalmic diseases or disorders in a subject, wherein said ophthalmic disease or disorder is morbus Stargardt.

In a further particularly preferred embodiment, the present invention provides a pharmaceutical combination described herein or a compound of formula I, or a pharmaceutically acceptable salt thereof for use in a method of preventing or treating ophthalmic diseases or disorders in a subject, wherein said ophthalmic disease or disorder is retinitis pigmentosa (retinopathia pigmentosa).

In a further particularly preferred embodiment, the present invention provides a pharmaceutical combination described herein or a compound of formula I, or a pharmaceutically acceptable salt thereof for use in a method of preventing or treating ophthalmic diseases or disorders in a subject, wherein said ophthalmic disease or disorder is diabetic retinopathy (retinopathia diabetica).

In the most preferred embodiment, the present invention provides a pharmaceutical combination described herein or a compound of formula I, or a pharmaceutically acceptable salt thereof for use in a method of preventing or treating ophthalmic diseases or disorders in a subject, wherein said ophthalmic disease or disorder is wet (exudative) age-related macular degeneration.

In one embodiment, the present invention provides a pharmaceutical combination comprising:
(a) a PPAR agonist;
(b) a p38 kinase inhibitor; and optionally
(c) one or more pharmaceutically acceptable diluents, excipients or carriers for use in a method of preventing or treating ophthalmic diseases or disorders in a subject, wherein said p38 kinase inhibitor is preferably inhibiting p38-alpha, p38-beta, p38-gamma or p38-delta or combinations thereof; more preferably inhibiting p38-alpha and/or p38-beta.

In one embodiment, the present invention provides a pharmaceutical combination comprising:
(a) a PPAR agonist;
(b) a p38 kinase inhibitor; and optionally
(c) one or more pharmaceutically acceptable diluents, excipients or carriers for use in a method of preventing or treating ophthalmic diseases or disorders in a subject, wherein said p38 kinase inhibitor is selected from the group consisting of pamapimod, acumapimod, losmapimod, dilmapimod, semapimod, AZD7624, ARRY-371797, LY2228820, R9111, PH-797804, BIRB 796, VX-702, VX-745 SB 239063, SB202190, SCIO 469, and BMS 582949 or a pharmaceutically acceptable salt thereof.

In a further embodiment, the present invention provides a pharmaceutical combination according to the invention, comprising
(a) a PPAR agonist;
(b) a compound of formula I as defined herein; and optionally
(c) one or more pharmaceutically acceptable diluents, excipients or carriers for use in a method of preventing or treating ophthalmic diseases or disorders in a subject.

In a further embodiment, the present invention provides a pharmaceutical combination comprising
(a) a PPAR agonist;
(b) a compound of formula II as defined herein; and optionally (c) one or more pharmaceutically acceptable diluents, excipients or carriers for use in a method of preventing or treating ophthalmic diseases or disorders in a subject.

In a preferred embodiment, the present invention provides a pharmaceutical combination comprising:
(a) a PPAR agonist;
(b) pamapimod or a pharmaceutically acceptable salt thereof; and optionally
(c) one or more pharmaceutically acceptable diluents, excipients or carriers for use in a method of preventing or treating ophthalmic diseases or disorders in a subject.

In a further embodiment, the present invention provides a pharmaceutical combination comprising
(a) a PPAR gamma agonist;
(b) a compound of formula I as defined herein; and optionally
(c) one or more pharmaceutically acceptable diluents, excipients or carriers for use in a method of preventing or treating ophthalmic diseases or disorders in a subject.

In a further embodiment, the present invention provides a pharmaceutical combination comprising
(a) a PPAR gamma agonist;
(b) a compound of formula II as defined herein; and optionally
(c) one or more pharmaceutically acceptable diluents, excipients or carriers for use in a method of preventing or treating ophthalmic diseases or disorders in a subject.

In a preferred embodiment, the present invention provides a pharmaceutical combination comprising
(a) a PPAR gamma agonist;
(b) a compound of formula I as defined herein; and optionally
(c) one or more pharmaceutically acceptable diluents, excipients or carriers for use in a method of preventing or treating ophthalmic diseases or disorders in a subject; wherein said PPAR gamma agonist is selected from the group consisting of pioglitazone, rosiglitazone, troglitazone and INT131 or a pharmaceutically acceptable salt thereof; and
wherein $X^1$ and $X^2$ in said compound of formula I are each O; and
wherein Z in said compound of formula I is N; and
wherein W in said compound of formula I is NH; and
wherein $A^1$ in said compound of formula I is aryl; and
wherein $R^1$ in said compound of formula I is heteroalkyl; and
wherein $R^3$ in said compound of formula I is alkyl.

In a further preferred embodiment, the present invention provides a pharmaceutical combination comprising
(a) a PPAR gamma agonist;
(b) pamapimod, R9111, semapimod, or a pharmaceutically acceptable salt thereof, preferably pamapimod or a pharmaceutically acceptable salt thereof; and optionally
(c) one or more pharmaceutically acceptable diluents, excipients or carriers for use in a method of preventing or treating ophthalmic diseases or disorders in a subject; wherein said PPAR gamma agonist is selected from the group consisting of pioglitazone, troglitazone, bezafibrate and pharmaceutically acceptable salts thereof.

In one embodiment, the present invention provides a pharmaceutical combination comprising:
(a) a PPAR agonist;
(b) a p38 kinase inhibitor; and optionally
(c) one or more pharmaceutically acceptable diluents, excipients or carriers for use in a method of preventing or treating ophthalmic diseases or disorders in a subject, wherein said PPAR agonist is activating PPAR alpha, PPAR gamma or PPAR delta or combinations thereof.

In one embodiment, the present invention provides a pharmaceutical combination comprising:
(a) a PPAR agonist;
(b) a p38 kinase inhibitor; and optionally
(c) one or more pharmaceutically acceptable diluents, excipients or carriers for use in a method of preventing or treating ophthalmic diseases or disorders in a subject, wherein said PPAR agonist is selected from the group consisting of pioglitazone, troglitazone, rosiglitazone, bezafibrate, fenofibrate, clofibrate, gemfibrozil, aleglitazar, muraglitazar, tesaglitazar, ragaglitazar, saroglitazar, GFT505, naveglitazar, GW501516 and INT131 or a pharmaceutically acceptable salt thereof.

In one embodiment, the present invention provides a pharmaceutical combination comprising:
(a) a PPAR agonist;
(b) a p38 kinase inhibitor; and optionally
(c) one or more pharmaceutically acceptable diluents, excipients or carriers for use in a method of preventing or treating ophthalmic diseases or disorders in a subject, wherein said PPAR agonist is selected from the group consisting of pioglitazone, troglitazone, bezafibrate and pharmaceutically acceptable salts thereof.

In a preferred embodiment, the present invention provides a pharmaceutical combination comprising:
(a) a PPAR agonist;
(b) a p38 kinase inhibitor; and optionally
(c) one or more pharmaceutically acceptable diluents, excipients or carriers for use in a method of preventing or treating ophthalmic diseases or disorders in a subject, wherein said PPAR agonist is pioglitazone or a pharmaceutically acceptable salt thereof.

In a further preferred embodiment, the present invention provides a pharmaceutical combination comprising:
(a) pioglitazone or a pharmaceutically acceptable salt thereof;
(b) a p38 kinase inhibitor; and optionally
(c) one or more pharmaceutically acceptable diluents, excipients or carriers for use in a method of preventing or treating ophthalmic diseases or disorders in a subject.

In a further preferred embodiment, the present invention provides a pharmaceutical combination comprising:
(a) pioglitazone hydrochloride;
(b) a p38 kinase inhibitor; and optionally
(c) one or more pharmaceutically acceptable diluents, excipients or carriers for use in a method of preventing or treating ophthalmic diseases or disorders in a subject.

In a particularly preferred embodiment, the present invention provides a pharmaceutical combination comprising:
(a) pioglitazone or a pharmaceutically acceptable salt thereof, preferably pioglitazone hydrochloride;
(b) pamapimod or a pharmaceutically acceptable salt thereof; and optionally
(c) one or more pharmaceutically acceptable diluents, excipients or carriers for use in a method of preventing or treating ophthalmic diseases or disorders in a subject.

In a further particularly preferred embodiment, the present invention provides a pharmaceutical combination comprising:
(a) pioglitazone or a pharmaceutically acceptable salt thereof, preferably pioglitazone hydrochloride;
(b) pamapimod or a pharmaceutically acceptable salt thereof; and optionally
(c) one or more pharmaceutically acceptable diluents, excipients or carriers for use in a method of preventing or treating ophthalmic diseases or disorders in a subject, wherein said ophthalmic diseases or disorders is Crohn's disease or ulcerative colitis.

EXAMPLES

The present Examples are intended to illustrate the present invention without restricting it.

Example 1: Synergistic Protection Conferred by the Combination of a PPAR Agonist and P38 Inhibitor to Prevent Choroidal Neovascularization in a Mouse Model of Age-Related Macular Degeneration (AMD)

Summary

CNV (choroidal neovascularization) in mice or rats is an accepted model to mimic the wet form of age-related macular degeneration (AMD). The model is induced by laser photocoagulation which creates breaks in Bruchs membrane. The subsequent pathological cascade includes inflammation, angiogenesis and proteolysis.

A study in a mouse model was performed to evaluate the efficacy of pioglitazone and pamapimod each alone or in combination on the development of CNV. Three laser burns were used to induce CNV in the eyes of C57Bl/6J mice. Pioglitazone or pamapimod or the combination of pioglitazone/pamapimod were administered orally once daily to groups of animals starting one day prior to lasering. After 14 days of treatment, the combination of pioglitazone/pamapimod reduced new vessel area and reduced retinal thickness in the CNV area more than either agent alone. These data support the potential for greater efficacy of the combination of a PPAR agonist (pioglitazone) and a P38 inhibitor (pamapimod) in the treatment of AMD and related eye diseases.

Methods

Animal Procedures

All animals were treated in accordance with the ARVO Statement for the Use of Animals in Ophthalmic and Vision Research and the EC Directive 86/609/EEC for animal experiments, using protocols approved and monitored by the Animal Experiment Board of Finland (Experimentica Ltd. animal license number ESAVI/219/04.10.07/2014).

Male 7-week old C57BL/6J mice (Janvier Labs, France) were obtained and housed at a constant temperature (22±+1° C.) in a light-controlled environment with ad libitum access to food and water.

For CNV induction, animals were anesthetized with an intraperitoneal injection of ketamine (37.5 mg/kg; Ketalar, Pfizer Oy Animal Health, Helsinki, Finland) and medetomidine (0.45 mg/kg; Domitor, Orion Oy, Espoo, Finland). A drop of 0.5% tropicamid (Santen) was applied on the cornea to dilate the pupils. Laser photocoagulation was performed once using a 532 nm diode laser Lumenis Novus Spectra (Lumenis Ltd., Israel) attached to a slit lamp. A coverslip and Viscotears® gel (Novartis) were used to applanate the cornea. Three laser lesions were performed per eye. Following lasering, anesthesia was reversed by u2-antagonist medetomidine, atipamezole (0.5 mg/kg i.p., Antisedan, Orion Pharma, Espoo, Finland).

Drug Treatment

Oral drug formulations were prepared in a vehicle adjusted to 4.8±0.05 using buffer. Test compounds [pioglitazone HCl (2.5 mg/ml), pamapimod (10 mg/ml) and combination pioglitazone HCl (2.5 mg/ml)+pamapimod (10 mg/ml)] were formulated in this vehicle and sonicated prior to administration (approx. 3 min).

Aflibercept (Eylea®, Bayer Pharma AG) was purchased as a ready-to-use solution for intravitreal injections at a concentration of 40 mg of aflibercept in 1 ml solution. The dose of 80 µg (injection volume of 2 µl) of aflibercept per mouse eye was used in the present study.

Compounds were administered either orally by gastric lavage (pioglitazone, pamapimod) at a dose of 0.2 ml volume per 20 g mouse weight or by IVT (aflibercept) using a 5 µl glass microsyringe (Hamilton Bonaduz AG, Bonaduz, Switzerland). Aflibercept was injected only into the lasered right eye. The injection volume was 2 µl per eye.

In Vivo Imaging

CNV lesions were monitored using Envisu R2200 SD-OCT (Spectral Domain Optical Coherence Tomography system; Bioptigen Inc./Leica) in anesthetized mice as described above. The thickness of each retina was measured from 24 sites of randomly overlaid grid and at all three lasered sites. The total retinal thickness was considered as the thickness of all layers from nerve fiber layer to RPE (healthy measurement sites) or to an implied line connecting the RPE around the site of damage (lasered sites).

Tissue Collection and Staining

At the end of the study, the mice were sacrificed by transcardial perfusion first with 0.9% NaCl solution, then with 4% paraformaldehyde in 0.1M phosphate buffer solution, pH 7.4. The eyes were collected and choroidal flat-mounts were prepared from each treated eye and fifteen (15) control eyes (three samples from each treatment group).

The flat-mount choroids were stained with fluorescein-labeled isolectin B4 (Vector Laboratories) to detect lesion CNV area and imaged using Leica DM IRBE microscope (Leica Microsystems, Germany) with an epifluorescent attachment and analyzed using Image J software (v.1.51f, National Institutes of Health, USA).

Data Analysis

Quantitative data was graphed and analyzed using GraphPad Prism software (v. 7.0, GraphPad Software Inc.). The D'Agostino & Pearson normality test was used for each parameter. Data that passed normality test were analyzed using One-Way ANOVA test with Tukey test for multiple comparisons, whereas Kruskal-Wallis test was applied for data that did not pass normality test with Dunn's post-hoc test for multiple comparisons. Differences were considered to be statistically significant at the $P<0.05$ level.

Results

Retinal thickness: Vehicle treated animals showed a marked increase in retinal thickness in the CNV area compared to total retinal thickness in non-CNV areas. All treatments, in comparison to vehicle, demonstrated lesser increases in CNV area retina thickness, consistent with reduced neovascularization (FIG. 1 and Table 1). The combination of pioglitazone and pamapimod was most efficacious, showing a small increase of 7.03±9.0% in CNV area retinal thickness vs. 7.75±22.4% and 9.86±17.7% for pamapimod alone and pioglitazone alone, respectively. Notably, pamapimod and pioglitazone, alone and in combination, were superior to the positive control Aflibercept (16.1±26.7).

Figure 2:
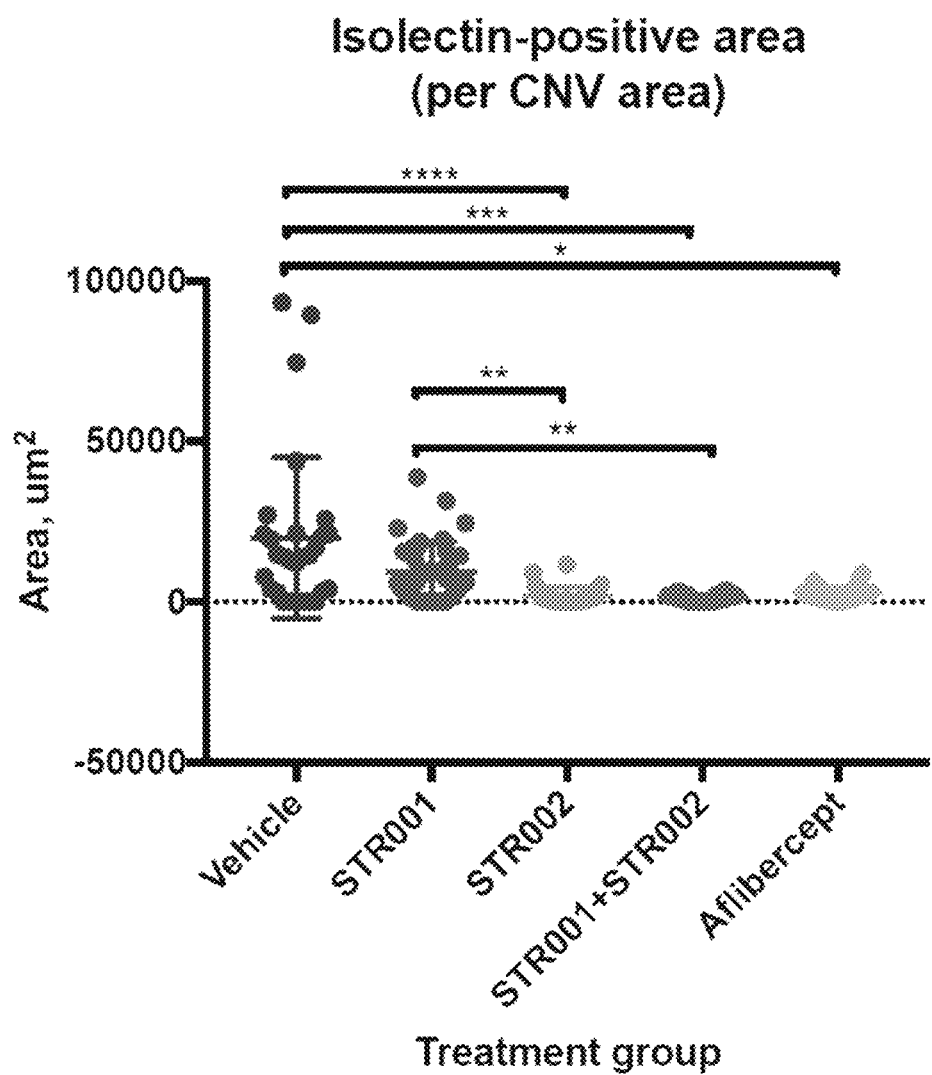
FIG. 2 shows isolectin-positive area as determined in each CNV lesion site (Kruskal-Wallis test followed by Dunn's multiple comparisons test, *P=0.025, P<0.07, *P=0.0001, ****P<0.0001). (STR001=pioglitazone HCl; STR002=pamapimod).

Chroidal CNV Area: Choroidal flatmounts were prepared and stained with isolectin B4 to identify endothelial cells in new vessels. CNV lesion sites were imaged using Image J software (v. 1.51f) to calculate the area of positive staining. FIG. 2 shows the isolectin B4 positive area per CNV lesion. The combination of pioglitazone/pamapimod showed the greatest reduction in the isolectin B4 staining area as compared to other treatments and the vehicle group. Pamapimod and pioglitazone/pamapimod were significantly different from the pioglitazone alone group (Kruskal-Wallis test followed by Dunn's multiple comparisons test, $P=0.0024$ and $P=0.0069$, respectively).

TABLE 1

Total retinal thickness and difference in retinal thickness in the CNV area as compared to the total retinal thickness.

| Group | Vehicle | STR001 | STR002 | STR001/STR002 | Aflibercept |
|---|---|---|---|---|---|
| Total retinal thickness, μm | 221 ± 2.9 (n = 10 eyes) | 215.8 ± 2.9 (n = 12 eyes) | 216.2 ± 6.0 (n = 10 eyes) | 216.8 ± 4.4 (n = 10 eyes) | 215.7 ± 6.5 (n = 10 eyes) |
| Difference in retinal thickness in CNV area, % | 19.9 ± 20.7 (n = 30 lesions) | 9.86 ± 17.7 (n = 36 lesions) | 7.75 ± 22.4 (n = 30 lesions) | 7.03 ± 9.0 (n = 30 lesions) | 16.1 ± 26.7 (n = 30 lesions) |

(STR001 = pioglitazone HCl; STR002 = pamapimod)
Data are expressed as mean ± SD (N of eyes)

CONCLUSIONS

All treatments (pioglitazone, pamapimod, pioglitazone/pamapimod and aflibercept) significantly decreased the formation of CNV in mice. The combination of pioglitazone/pamapimod reduced new vessel area as determined by immunohistochemical analysis (isolectin B4 staining) in a synergistic manner and also reduced retinal thickness in the CNV area more than either agent alone. These data support the potential for greater and synergistic efficacy of the combination of a PPAR agonist (pioglitazone) and a P38 inhibitor (pamapimod) in the treatment of AMD and related eye diseases.

The invention claimed is:

1. A method of preventing or treating ophthalmic diseases or disorders, wherein said ophthalmic disease or disorder is macular degeneration, comprising administering a pharmaceutical combination comprising:
   (a) a PPAR agonist;
   (b) a p38 kinase inhibitor; and optionally
   one or more pharmaceutically acceptable diluents, excipients or carriers to a subject in need thereof, wherein said PPAR agonist is pioglitazone or a pharmaceutically acceptable salt thereof, and said p38 kinase inhibitor is pamapimod or a pharmaceutically acceptable salt thereof.

2. The method according to claim 1, wherein said combination is administered orally to the subject.

3. The method according to claim 1, wherein said macular degeneration is age-related macular degeneration (AMD).

* * * * *